(12) United States Patent
Martin et al.

(10) Patent No.: US 12,023,205 B2
(45) Date of Patent: Jul. 2, 2024

(54) BREAKAGE DETECTION OF TENSION ELEMENT FOR COUNTERBALANCE MECHANISM

(71) Applicant: Intuitive Surgical Operations, Inc., Sunnyvale, CA (US)

(72) Inventors: David F. Martin, Santa Clara, CA (US); Lawton N. Verner, San Jose, CA (US); Hsien-Hsin Liao, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 547 days.

(21) Appl. No.: 17/234,655

(22) Filed: Apr. 19, 2021

(65) Prior Publication Data

US 2021/0322127 A1    Oct. 21, 2021

Related U.S. Application Data

(60) Provisional application No. 63/012,541, filed on Apr. 20, 2020.

(51) Int. Cl.
*A61B 90/00* (2016.01)
*A61B 34/35* (2016.01)
(Continued)

(52) U.S. Cl.
CPC ............. *A61B 90/06* (2016.02); *A61B 34/35* (2016.02); *A61B 90/50* (2016.02); *G01D 5/145* (2013.01);
(Continued)

(58) Field of Classification Search
CPC ......... A61B 90/06; A61B 34/35; A61B 90/50; A61B 2034/715; A61B 2090/064;
(Continued)

(56) References Cited

U.S. PATENT DOCUMENTS 8,220,765 B2    7/2012  Bailey
8,490,953 B2    7/2013  Luke et al.
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Xin Y Zhong
(74) *Attorney, Agent, or Firm* — IP Spring

(57) ABSTRACT

Implementations relate to breakage detection of a tension element for a counterbalance mechanism. In some implementations, a tension element breakage detection mechanism includes a tension element, a moveable detection element contacting the tension element, and an actuator. The moveable detection element is biased by the tension element toward a first configuration in a range of motion of the moveable detection element. The moveable detection element is biased toward a second configuration in the range of motion of the moveable detection element by a force generated by the actuator on the moveable detection element. The breakage detection mechanism includes a sensor of a change of the moveable detection element from the first configuration to the second configuration, the change being in response to breakage of the tension element.

20 Claims, 13 Drawing Sheets

(51) Int. Cl.
*A61B 90/50* (2016.01)
*G01D 5/14* (2006.01)
*A61B 34/00* (2016.01)

(52) U.S. Cl.
CPC ... *A61B 2034/715* (2016.02); *A61B 2090/064* (2016.02); *A61B 2090/5025* (2016.02)

(58) Field of Classification Search
CPC .... A61B 2090/5025; A61B 2090/0809; A61B 34/76; A61B 34/74; G01D 5/145
See application file for complete search history.

(56) References Cited

U.S. PATENT DOCUMENTS

| | | |
|---|---|---|
| 9,050,119 B2 | 6/2015 | Devengenzo et al. |
| 9,301,807 B2 | 4/2016 | Duval |
| 9,850,994 B2 | 12/2017 | Schena et al. |
| 9,877,792 B2 | 1/2018 | Cooper et al. |
| 2009/0322001 A1* | 12/2009 | Luke ................. F16F 15/28 267/71 |

* cited by examiner

BREAKAGE DETECTION OF TENSION ELEMENT FOR COUNTERBALANCE MECHANISM

CROSS-REFERENCE TO RELATED APPLICATIONS

The present application claims priority to U.S. Provisional Patent Application No. 63/012,541, filed Apr. 20, 2020 and titled "Break Detection of Tension Element for Counterbalance Mechanism," the entire contents of which are hereby incorporated by reference.

BACKGROUND

Load positioning systems can be used in a variety of applications. In one example, a control input device can include a grip held by a user, where the grip is connected to a mechanical linkage such as a mechanical arm. The grip can be moved by the user in one or more degrees of freedom provided by the mechanical arm to provide input to a system, such that the user contact on the grip acts as a load on the mechanical arm. In some examples, the grip is included in a control input device that can be manipulated by a user to control functions of a slave or manipulator device, including movement and other operations of the slave device. For example, forces can be applied to the mechanical arm by motors to provide force feedback to the control input device and/or to position the grip in a particular workspace. For example, master control devices can be used in master-slave systems such as teleoperated surgical devices that allow the user to control various types of slave medical instruments at a surgical site to perform surgical procedures. Other master-slave systems can also make use of control input devices to allow a user to control one or more slave devices at a worksite. In other examples, load positioning systems can be provided at the slave device of a teleoperated system, e.g., at mechanical linkages of the slave device used to move and hold various end effectors such as surgical instruments or other tools. Further, load positioning systems can be used in other types of control input devices that are not part of a master-slave system.

In some implementations of load positioning systems, a counterbalance force is applied to the mechanical arm by a counterbalance mechanism to compensate for the effects of gravity on the mechanical arm. For example, the counterbalance mechanism can include springs that provide the counterbalance force. The use of a counterbalance mechanism allows gravity compensation when the motors are not powered, and allows forces of lower magnitude to be output by the motors applying forces to the mechanical arm since the motors need not provide as much counterbalance forces themselves to compensate for gravity. In one example, the counterbalance mechanism may provide a reduction in the speed and/or magnitude of motion of the arm falling through space, e.g., when the user removes his or her grip from an input control device connected to the arm.

Some types of counterbalance mechanisms use one or more cables to connect the mechanical arm to the spring that provides the counterbalance force. A disadvantage to using such a mechanism is that a mechanical failure such as cable breakage may cause the counterbalance mechanism to fail, which in turn causes an immediate effect of gravity on the load. For example, a cable break can cause a control input device to suddenly move downward under gravity since the counterbalance force is removed. Such a failure can be dangerous in some applications such as teleoperated surgery, where the undesired movement of a control input device may pull on a user's hand and/or cause corresponding undesired movement of a surgical tool or other end effector during a surgical procedure.

Some systems have included systems to reduce the effects of such a cable break in a counterbalance mechanism. For example, redundant or doubled cables can be used to reduce the chances of overall failure. Some systems include a cable breakage detection mechanism, so that, for example, control of slave devices by a control input device is immediately terminated upon detection of a cable break. In some of these systems, an encoder senses rotation of a pulley caused by movement of the cable of the counterbalance system when the mechanical arm is moved. A specific motion of the pulley is expected based on the expected motion of the cable and arm. An unexpected sensed motion (or lack of motion) of the pulley during sensed motion of the arm indicates a potential cable break.

However, this cable breakage detection can require running a process that is continuously determining rotation of a pulley, comparing current pulley rotation to expected rotation, and/or determining change in motion of a pulley to detect an anomalous change in cable movement. This may be undesirable in some cases, e.g., in particular operating modes of a mechanical system. Furthermore, in some systems there can be movement ranges of the mechanical arm in which the cable slows and reverses its direction of travel, such that cable movement may be greatly reduced or not occur. At the point of direction reversal, the sensitivity of detecting a cable failure may be lower due to the small motion of the cable with respect to a large motion of the arm, potentially causing reduced ability to detect a cable break in such ranges of movement of a mechanical linkage.

SUMMARY

Implementations of the present application relate to detection of a break of a tension element in a counterbalance mechanism. In some implementations, a tension element breakage detection mechanism includes a tension element and a moveable detection element contacting the tension element. The moveable detection element is biased, by the tension element, toward a first configuration in a range of motion of the moveable detection element. An actuator is coupled to the moveable detection element, the moveable detection element being biased toward a second configuration in the range of motion of the moveable detection element by a force generated by the actuator on the moveable detection element. The mechanism includes a sensor of a change of the moveable detection element from the first configuration to the second configuration in the range of motion of the moveable detection element, the change being in response to breakage of the tension element.

Various implementations and examples of the tension element breakage detection mechanism are described. For example, in some implementations, the tension element is coupled to a counterbalance spring. In some implementations, the tension element has a first end coupled to the counterbalance spring and the tension element has a second end coupled to the moveable detection element. In some implementations, a load is moveably coupled to the moveable detection element, and the load includes at least one mechanical member of a mechanical arm. In some implementations, the tension element is a cable including two doubled portions provided between the counterbalance spring and the moveable detection element. In some implementations, a tension pulley around which the tension element is at least partially wrapped, the tension pulley positioned between the counterbalance spring and the moveable detection element in a path of the tension element. In some implementations, the tension element is one of a cable, belt, or chain. In various implementations, the actuator is a spring, e.g., a torsion spring. In some implementations, the tension element breakage detection mechanism is embodied in a counterbalance apparatus included in a component of a teleoperated surgical system. In some implementations, the tension element is a cable, the moveable detection element includes a detection pulley, and the cable is coupled to the detection pulley and causes rotation of the detection pulley in response to movement of the cable along a lengthwise axis of the cable.

In some implementations, the force generated by the actuator is a second force, and a first force is applied to the moveable detection element via the tension element, the first force biasing the moveable detection element toward the first configuration in the range of motion of the moveable detection element. In some implementations, the moveable detection element includes a detection pulley, the first configuration is a first orientation of the detection pulley about a rotational axis of the detection pulley, the second configuration is a second orientation of the detection pulley about the rotational axis of the detection pulley, the first force is a first torque in a first rotational direction that biases the detection pulley toward the first orientation, the second force is a second torque in a second rotational direction opposite to the first rotational direction that biases the detection pulley toward the second orientation, and the first torque has a first magnitude and the second torque has a second magnitude, the first magnitude being greater than the second magnitude. In some implementations, the tension element is a cable, the detection pulley is at the first orientation while the cable is in an unbroken state, and the detection pulley is at the second orientation in response to the first magnitude of the first torque becoming lower than the second magnitude of the second torque caused by breaking of the cable.

In some implementations, the second force causes the moveable detection element to move to the second configuration on condition of at least a threshold reduction of the first force caused by breaking of the tension element, and the threshold reduction of the first force is such that the first force has a magnitude less than a magnitude of the second force. In some implementations, the moveable detection element is rotatably coupled to a first member of a mechanical linkage, the tension element is coupled between the first member and a second member of the mechanical linkage, and a load is coupled to the moveable detection element, the load including at least one member of the mechanical linkage. In some implementations, the breakage detection mechanism further includes a first member, a second member coupled to the first member, a counterbalance spring coupled to the first member, and a tension pulley rotatably coupled to the second member, wherein the moveable detection element is a detection pulley that is rotatably coupled to the first member, the actuator is coupled between the detection pulley and the first member, the tension element has a first end coupled to the counterbalance spring and a second end coupled to the detection pulley, the tension element is coupled between the first member and the second member, the tension element is wrapped around at least a portion of the tension pulley and wrapped around at least a portion of the detection pulley, and the tension element applies a counterbalance force to the second member.

In some implementations, a first stop is positioned in the range of motion of the moveable detection element against which the moveable detection element is biased at the first configuration, and a second stop is positioned in the range of motion of the moveable detection element against which the moveable detection element is biased at the second configuration. In some implementations, the moveable detection element includes a pulley and a linear member, the pulley is rotatably coupled to the linear member, the linear member is coupled to the actuator, and the moveable detection element has a linear range of motion. In some examples, the actuator generates the force as a linear force on the linear member, the tension element, in an unbroken state, contacts the pulley, and the tension element biases the moveable detection element by opposing the linear force generated by the actuator to cause the linear member to be positioned in the first configuration. In some implementations, an opposing force is applied to the moveable detection element via the tension element, the opposing force biasing the moveable detection element toward the first configuration in its linear range of motion, and the linear force causes the moveable detection element to move to the second configuration on condition of at least a threshold reduction of the opposing force caused by breaking of the tension element and in which the opposing force has a magnitude less than a magnitude of the linear force.

In some implementations, an apparatus to detect breakage of a tension element in a counterbalance mechanism includes a moveable detection element coupled to a first member of a mechanical linkage. In some implementations, a method to detect breakage of a tension element coupled to a counterbalance spring in a counterbalance mechanism includes applying, by the tension element, a first force to a detection element in a first direction to cause a first configuration of the detection element; applying, by an actuator, a second force to the detection element in a second direction opposite to the first direction; moving, by the second force, the detection element to a second configuration in response to at least a threshold reduction of the first force caused by breaking of the tension element; and sensing a change of the detection element from the first configuration to the second configuration.

DETAILED DESCRIPTION

Figure 1:
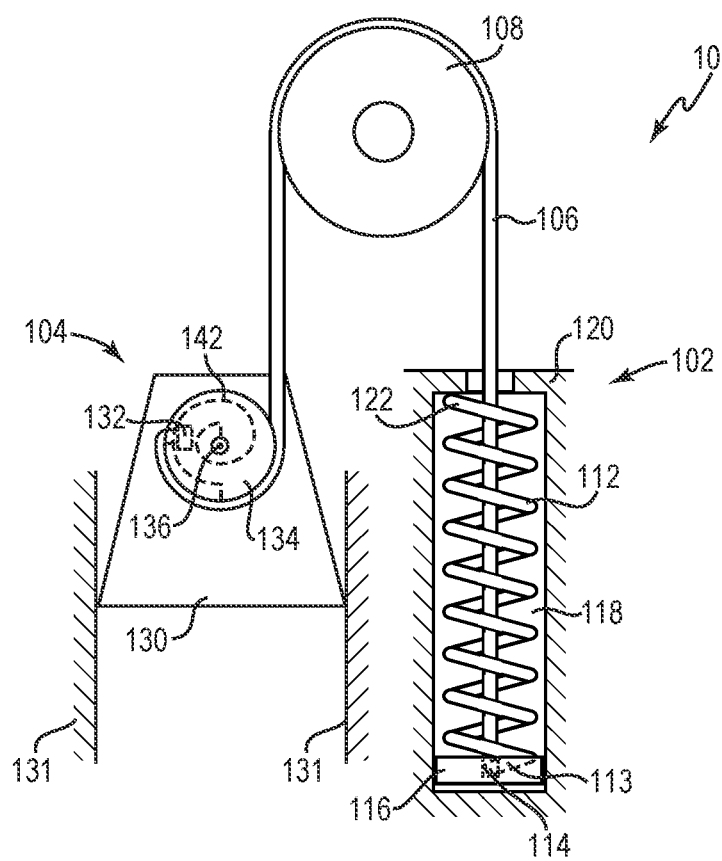
FIG. 1 is a diagrammatic illustration of a counterbalance mechanism including one or more tension element break detection features, according to some implementations.

Implementations described herein relate to detection of breakage of a tension element in a counterbalance mechanism. In some implementations, a tension element break detection mechanism is included in a counterbalance mechanism and detects a break of a tension element such as a cable. A counterbalance spring provides force on a load such as a mechanical linkage, e.g., to oppose gravity. The apparatus includes a moveable detection element, e.g., a detection pulley rotatably coupled to a member of the mechanical linkage, or a pulley/member that can linearly move with respect to the mechanical linkage. The detection element is movable between a first configuration (e.g., first orientation or position) and a second configuration (e.g., second orientation or position). The tension element, such as a cable, can be coupled between the first member and a second member of the mechanical linkage and contacts the detection element, which maintains the detection element at the first orientation. In response to breakage of the tension element, the detection element is moved from the first configuration to the second configuration, and a sensor senses this change of the detection element to sense the breakage of the tension element.

Various features of the tension element breakage detection mechanism are disclosed. For example, the detection element can include a detection pulley, and the tension element can apply a first torque to the detection pulley in a first rotational direction to bias the detection pulley toward the first orientation. The first torque corresponds to a first force applied to the tension element, e.g., due to gravity. An actuator, such as a spring (e.g., torsion spring), can be coupled between the detection pulley and the first member, to generate second torque on the detection pulley in a second rotational direction toward the second orientation of the pulley. The second torque is configured to cause the detection pulley to rotate to the second orientation in response to a particular reduction of the first torque caused by the breakage of the cable. For example, the first force has a first magnitude that is greater than a second magnitude of the second force. The second torque causes the detection pulley to rotate to the second orientation if at least a threshold reduction of the first torque is caused by the breaking of the tension element, resulting in the first torque having a magnitude less than the second torque. In some implementations, a first stop is positioned in the range of motion of the detection pulley against which the pulley is biased at the first orientation, and a second stop is positioned in the range of motion against which the detection pulley is biased at the second configuration.

In other features, the detection element can include a linear member and/or a detection pulley, and the tension element can apply a first linear force to the detection element in a first linear direction to bias the detection element toward a first position. An actuator, such as a spring, can be coupled to the detection element to generate a second linear force on the detection pulley in a second linear direction toward a second position. The second linear force is configured to cause the detection element to move to the second position in response to a particular reduction of the first linear force caused by the breakage of the cable.

In some examples, if a breakage of the tension element (such as a cable) occurs, the counterbalance mechanism provides reduced or no gravity compensation to a connected control input device, which may cause undesired forces on or movement of the control input device. The described features allow a control circuit to, in response to detecting a cable break, immediately deactivate a controlling mode in which the control input device controls a manipulator device (e.g., slave device) and activate a non-controlling mode in which the control input device no longer controls the manipulator device. This reduces or eliminates uncontrolled and undesired movement in a controlled manipulator device that may occur from counterbalance mechanism cable failure. In some implementations, the system can deactivate actuators outputting force on the control input device in response to detecting a cable break, thus increasing safety for the operator of the control input device.

Features described herein enable robust detection of tension element breakage in a counterbalance mechanism. In some examples, tension element breakage can be detected without requiring continuous determination and comparison of pulley orientation or rotation to previous orientations. For example, in some described features, a tension element break causes a particular rotation (or other movement) of a detection pulley (or other detection element) that can be sensed in response to the break. Furthermore, tension element breaks can be reliably detected in particular movement ranges of a mechanical arm. For example, during arm movement in a particular range, the tension element may slow and reverse its direction of travel such that tension element movement may be greatly reduced or not occur. Described features allow tension element breakage to be robustly detected in such movement ranges, thus enhancing the reliability of tension element break detection.

The implementations described herein can be used in a variety of types of devices. In some examples, a described tension element breakage detection mechanism can be coupled to a mechanical linkage. In some examples, the mechanical linkage can be a mechanical arm that includes a handle or grip that is grasped by a user during operation. For example, the handle and mechanical arm may be included in or coupled to a control input device that can be manipulated by a user to control functions of a system. Motors or other actuators output force on the mechanical arm and/or can position the mechanical arm in a particular workspace. A counterbalance apparatus using features described herein can be coupled to the mechanical arm and provide counterbalance force to the mechanical arm and/or handle. In some examples, the control input device can be included or embodied in a user control system (e.g., console) of a teleoperated surgical system that allows the user to control manipulator arms and surgical instruments of a manipulator device located at a surgical site to perform surgical procedures. In some systems, the control input device can control any of various other functions or devices.

In other examples, implementations described herein can be included or embodied in a manipulator device of a teleoperated system that is controlled by a user control system. For example, in a teleoperated surgical system, the manipulator device can include one or more mechanical arms that hold any of various surgical instruments or other tools, and which can perform surgical procedures at a surgical site. Motors at the manipulator device move the mechanical arms, based on commands from the user control system, to positions and orientations at the surgical site. A counterbalance apparatus using features described herein can be coupled to the manipulator arm and provide counterbalance force to the manipulator arm and/or surgical instrument. The counterbalance apparatus described herein can alternatively be used in other types of systems and devices.

The terms "center," "parallel," "perpendicular," "orthogonal," "aligned," or particular measurements in degrees, Hertz, or other units as used herein need not be exact and can include typical engineering tolerances. Some implementations herein may relate to various objects in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded unit or device is constrained with respect to possible position and orientation motion in a large working environment (e.g., an operating area or room). Also, such a unit is kinematically coupled to the ground (e.g., mechanically supported by a console, supports, or other object attached to the ground). As used herein, the term "proximal" refers to an element that is close to (or closer to) a mechanical ground and the term "distal" refers to an element that is away from (or further from) a mechanical ground.

The term "torque" as used herein refers to rotational forces and/or refers to a context of rotational motion, and in various implementations using one or more described features, other types of forces can be used as appropriate in place of or in addition to torque, e.g., linear forces or other forces, and/or forces in a context of translational motion.

FIG. 1 is a diagrammatic illustration of a counterbalance mechanism 100 including one or more tension element break detection features, according to some implementations.

Counterbalance mechanism 100 includes a spring component 102 and a load component 104. A tension element 106 is fixedly coupled between spring component 102 and load component 104, and tension element 106 wraps around a tension pulley 108.

Spring component 102 includes a counterbalance spring 112 that provides a spring force on tension element 106. In the example shown, spring 112 is provided in a chamber 118 of a frame 120. In some examples, frame 120 can be a member that is mechanically grounded, or frame 120 can be part of a member in an arm linkage, as described in some examples herein.

In the example shown, spring 112 is used as a compression spring, and a first end 114 of tension element 106 is routed through the center of spring 112 and is coupled to a first end 113 of spring 112 furthest along the path of tension element 106, or is coupled to another portion of spring 112 that allows compression of at least part of spring 112 caused by movement of the first end 113 of spring 112 pulled by tension element 106 toward the load component 104. For example, first end 114 of tension element 106 can be coupled to a guide element 116 that engages the first end 113 of spring 112 and can move through cylindrical chamber 118. The movement of tension element 106 toward load component 104 causes guide element 116 in chamber 118 to compress spring 112, providing a spring force against movement of tension element 106 toward load component 104.

In some other implementations, spring 112 can be used as a tension or extension spring in counterbalance mechanism 100. For example, first end 114 of tension element 106 can be coupled to a second end 122 of spring 112 and first end 113 of spring 112 can be coupled to frame 120. In examples of these implementations, movement of tension element 106 toward load component 104 causes spring 112 to stretch, providing a spring force against movement of tension element 106 toward load component 104.

Load component 104 includes a load 130 that is being counterbalanced by counterbalance mechanism 100. For example, load 130 can be a portion of a mechanical member in a mechanical system, e.g., a mechanical member of an arm mechanism. For example, the mechanical member can be rotatably coupled to frame 120 as described in examples below. Load 130 can move in one or more degrees of freedom. In some implementations, the load 130 can translate but not rotate, as indicated by vertical guide 131 that allows vertical translation of load 130. Thus, detection pulley 134 (described below) can rotate as the load 130 moves (translates). Detection pulley 134 is rotatably coupled to load 130 and translates as load 130 translates, but rotates with respect to load 130 if the tension force in tension element 106 is removed (e.g. via breakage of tension element 106).

Load component 104 is coupled to a second end 132 of tension element 106, opposite to first end 114, via a tension element breakage detection element, which is shown in this example as a break detection pulley 134. Tension element 106 is at least partially wrapped around detection pulley 134. For example, tension element 106 can be terminated at second end 132 that is routed through an aperture in detection pulley 134.

Tension element 106 can be any flexible element that can be routed to and/or around the components of the counterbalance mechanism 100. For example, tension element 106 can be a flexible cable, e.g., a steel cable. In some implementations, tension element 106 can be a belt, chain, or other flexible element.

Tension pulley 108 can be positioned in the path of tension element 106, e.g., tension element 106 can be wrapped at least partially around tension pulley 108. In various implementations, tension pulley 108 can be located at different locations of a mechanical system being counterbalanced by counterbalance mechanism 100. For example, tension pulley 108 can be coupled to frame 120, or can be coupled to load component 130. In some implementations, multiple tension pulleys can be provided in the path of tension element 106, e.g., with tension element 106 wrapped at least partially around each such tension pulley.

Figure 2:
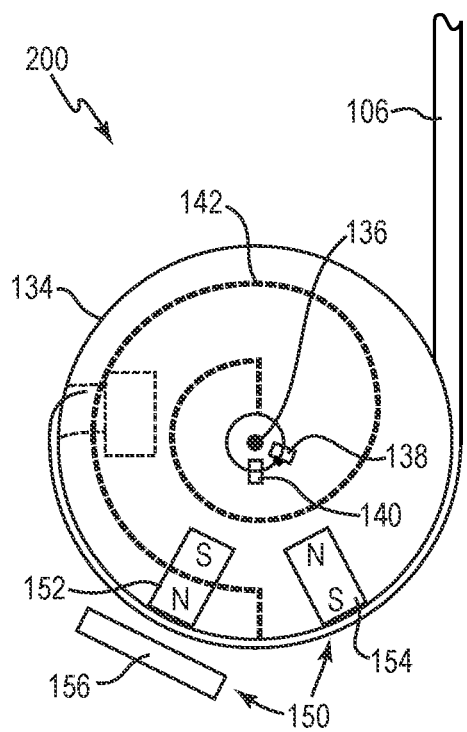
FIGS. 2 and 3 are diagrammatic illustrations showing a detection pulley system in two different sensed rotational orientations.
Figure 3:
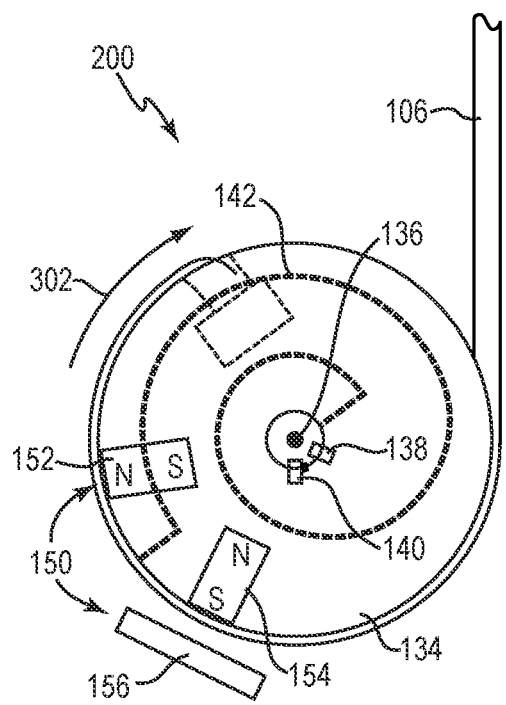

Detection pulley 134 is a breakage detection element that rotatably coupled to load 130 at an axis of rotation 136 of the detection pulley. Detection pulley 134 is used to detect a break in tension element 106 that may occur during operation of the counterbalance mechanism 100. A first torque is applied to detection pulley 134 in a first rotational direction that corresponds to a force applied to tension element 106 by counterbalance spring 112. For example, the first rotational direction is biased in the counterclockwise direction as shown in FIGS. 1-3 by tension element 106. Detection pulley 134 is rotatable about axis 136 in a rotational range constrained by a first stop and a second stop (examples shown in FIGS. 2-3). The first stop is provided in the range of rotation of detection pulley 134 such that the detection pulley cannot rotate past the first stop in the first rotational direction about axis 136. Similarly, the second stop is provided in the range of rotation of detection pulley 134 such that the detection pulley cannot rotate past the second stop in a second rotational direction about axis 136 that is opposite to the first rotational direction.

An actuator 142 is coupled between detection pulley 134 and load 130 and applies a force (torque) to detection pulley 134 to bias detection pulley 134 in a second rotational direction about axis 136 that is opposite to the first rotational direction. For example, actuator 142 can bias detection pulley 134 in the clockwise direction as shown in FIGS. 1-3, e.g., a direction from the first stop toward the second stop. Actuator 142 can be any device or element that applies such a force. In some examples, actuator 142 can be a spring, such as a torsion spring, that applies the force to the detection pulley 134. In some implementations, actuator 142 can be an active actuator, e.g., a motor.

A detection pulley sensor (examples shown in FIGS. 2-3) is coupled to load component 104 to sense movement or change of a detection element, e.g., sense rotation of detection pulley 134. For example, the detection pulley sensor can be a pulley orientation sensor that can sense rotational orientation, e.g., a change in rotational orientation, of detection pulley 134 about axis 136. In some examples, the detection pulley sensor includes one or more rotating sensor elements that are coupled to detection pulley 134 and one or more sensor elements that are coupled to load 130 that detect the presence of one of the rotating sensor elements. Alternatively, the one or more rotating sensor elements detect the presence of the one or more sensor elements coupled to load 130. Some examples of such a sensor are described with reference to FIGS. 2 and 3.

In various implementations, one or more of the pulleys of the counterbalance mechanism can include grooves on their circumferential surface, to cause tension element 106 to be more securely wrapped and engaged by the pulley, e.g., stay in place around the pulley. For example, in a system using a tension element that is a doubled cable (or two cables), a pulley (e.g., the detection pulley and/or other pulley(s)) can include a first groove and a second groove parallel to the first groove. A first portion of the doubled cable is wrapped at least partially around the pulley in the first groove and a second portion of the doubled cable (or second cable) is wrapped at least partially around the detection pulley in the second groove. In some implementations using other types of tension elements (e.g., a belt), the pulleys do not include such grooves, e.g., one or more pulleys can include flanges surrounding the belt to keep the belt in place around the pulleys.

FIGS. 2 and 3 are diagrammatic illustrations showing a detection pulley system 200 in two different sensed configurations, e.g., different rotational orientations. Pulley system 200 is described with reference to the counterbalance mechanism 100 of FIG. 1, but can also be used in counterbalance system 400 of FIG. 4 (described below) or other counterbalance systems.

In FIG. 2, tension element 106 of counterbalance mechanism 100 is operating in its normal, unbroken state. Detection pulley 134 is shown held in a first configuration (e.g., a first orientation in this example) about axis 136 against a first stop 138 by the tension element 106 while the counterbalance force from spring 112 is provided on tension element 106. First stop 138 stops rotation of detection pulley 134 in one rotational direction, e.g., the counterclockwise direction as shown in FIG. 2. First stop 138 can be implemented in various ways. For example, a shaft of detection pulley 134 can include first and second portions, such that the first portion is coupled to detection pulley 134 to rotate with pulley 134 with respect to the second portion. First stop 138 can include a member or surface of the second portion of the pulley shaft such that a member or surface of the first portion engages with the member or surface of the second portion to stop rotation in a particular direction (e.g., the counterclockwise direction in this example).

The first orientation of detection pulley 134, as shown in FIG. 2, is caused by tension from tension element 106 prevailing over the torque provided by actuator 142. For example, first torque applied to detection pulley 134 by tension element 106 has a higher magnitude than second torque applied to detection pulley 134 by actuator 142 in the opposite rotational direction about axis 136. The first torque applied to detection pulley 134 remains higher than the second torque from actuator 142 for any movement of the load 130 with respect to the tension pulley 108 and/or spring component 102, such that detection pulley 134 remains in the first orientation during normal operation of the mechanical system including frame 120 and load 130.

A sensor 150 is used to sense orientations of detection pulley 134. In this example, sensor 150 is a magnetic sensor, including rotating sensor elements 152 and 154 and a detection sensor element 156. Rotating sensor element 152 includes a first magnet and rotating sensor element 154 includes a second magnet. One of these magnets has a north pole closer to the outer edge of detection pulley 134 (and further from axis 136) than its south pole, and the other magnet has a south pole closer to the outer edge (and further from axis 136) than its north pole. Detection sensor element 156 can be, e.g., a Hall effect sensor, that can sense the presence (magnetic field) of one of the rotating sensor elements 152 or 154 that is positioned closest to it (e.g., the sensor can sense the closer element 152 or 154 more strongly than the other, further sensor element). For example, if one type of magnetic pole is detected, detection sensor element 156 outputs a first value, and if the other type of magnetic pole is detected, sensor element 156 outputs a second value. As shown in the example of FIG. 2, sensor 150 senses closer rotating element 152 (e.g., first magnet) continuously during standard operation of the counterbalance mechanism 100.

In some implementations, to sense redundancy, detection sensor element 156 includes multiple (e.g., two) sensors for each position of the detection element, e.g., for each detected orientation of detection pulley 134. For example, when sensor element 152 (e.g., north pole of a magnet) approaches detection sensing element 156 (or is closer to detection sensing element 156 than the other sensor element 154), a first sensor of detection sensor element 156 outputs a high signal and a second sensor of detection sensor element 156 outputs a low signal. Conversely, when sensor element 154 (e.g., south pole of a magnet) approaches or is closer to detection sensor element 156 than the other sensing element 152, the first sensor of sensor element 156 outputs a low signal and the second sensor of sensor element 156 outputs a high signal. Each signal can be checked by the system to sense and confirm the detected pulley orientation.

In some implementations, other types of sensors can be used to detect rotational orientation and/or rotation of detection pulley 134. For example, an optical sensor can be used, e.g., where rotating sensor elements 152 and 154 are optical emitters that emit different beams of electromagnetic energy sensed by detection sensor element 156, or the opposite configuration is used in which a sensor element 156 emits an electromagnetic beam and rotating sensor elements 152 and 154 are detectors. In some implementations, sensor element 156 can include both emitters and detectors, such that the detectors can detect a beam emitted by the emitters and reflected by a sensor element 152 or 154 (e.g., different amounts or patterns of reflection provided by sensor elements 152 and 154). In some implementations, one rotating sensor element can be detected by multiple sensor elements coupled to load 130. Other types of sensors that can be used include mechanical switches. For example, sensor element 156 can include a mechanical spring lead that contacts one of rotating sensor elements 152 or 154 to complete a circuit and sense the presence of the contacted rotating sensor element. Other types of sensors that can be used include inductive sensors that can detect metallic objects.

FIG. 3 shows detection pulley system 200 at a different rotational orientation. In FIG. 3, the counterbalance mechanism 100 includes tension element 106 in a broken state. Once tension element 106 breaks, the first torque provided by tension element 106 on detection pulley 134 is removed. This allows the second torque applied by actuator 142 to take effect and to rotate the detection pulley 134 about axis 136 in rotational direction 302, toward the second stop 140 (e.g., clockwise direction as shown in FIG. 3). The detection pulley 134 stops moving at a second configuration (e.g., a second orientation in this example) against the second stop 140. This rotation from the first orientation to the second orientation causes rotating element 152 to rotate away from the sensor element 156 (e.g., out of sensing range or to a position causing reduction of sensed magnitude of rotating element 152), and causes rotating element 154 to rotate within sensing range of the sensor element 156 or to a position having a higher magnitude sensed by the sensor element 156 than rotating element 152. The sensing of rotating element 154 causes a signal to be sent to a control circuit that indicates that breakage of tension element 106 has been detected. Sensor 150 senses the rotating element 154 continuously while the tension element 106 remains broken.

Figure 4:
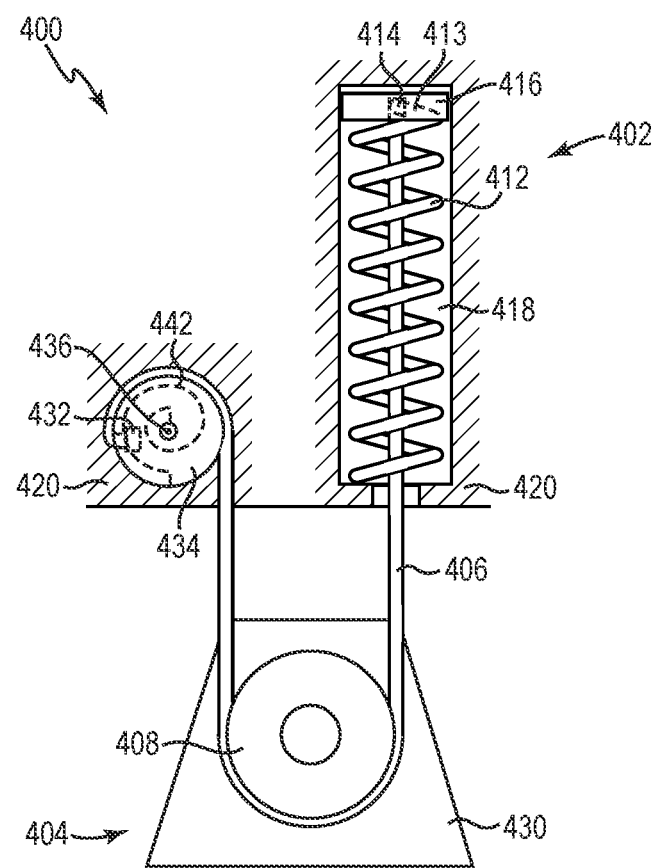
FIG. 4 is a diagrammatic illustration of another example counterbalance mechanism including one or more features described herein, according to some implementations.

FIG. 4 is a diagrammatic illustration of another example counterbalance mechanism 400 including one or more tension element breakage detection features described herein, according to some implementations. Counterbalance mechanism 400 includes a spring component 402 and a load component 404. A tension element 406 is fixedly coupled between spring component 402 and load component 404, where tension element 406 wraps around a tension pulley 408. Tension element 406 can be any flexible element similarly as described for FIG. 1.

Spring component 402 includes a counterbalance spring 412 that provides a spring force on tension element 406. In the example shown, spring 412 is provided in a chamber 418 of a frame 420. In some examples, frame 420 can be a member that is mechanically grounded, or frame 420 can be part of a member in an arm linkage, as described in some examples herein.

In the example shown, spring 412 is used as a compression spring similarly as described for FIG. 1. For example, a first end 414 of tension element 406 can be coupled to a guide element 416 that engages a first end 413 of spring 412 and can move along cylindrical chamber 418. The movement of tension element 406 toward load element 404 away from guide element 416 causes guide element 416 to move in chamber 418 and compress spring 412, providing a spring force against that movement of tension element 406. In some other implementations, spring 412 can be used as a tension spring in counterbalance mechanism 400 similarly as described for FIG. 1.

Load component 404 includes a load 430 that is being counterbalanced by the counterbalance mechanism 400. For example, load 430 can be part of a mechanical member, e.g., a mechanical member rotatably coupled to frame 420 as described in examples below. Load component 404 is coupled to tension element 406 via a tension pulley 408, and tension element 406 is wrapped at least partially around tension pulley 408. Tension pulley 408 is rotatably coupled to load 430. Tension pulley 408 is thus positioned in the path of tension element 406. In various implementations, multiple tension pulleys can be provided in the path of the tension element 406, e.g., with tension element 406 wrapped at least partially around each such tension pulley.

A second end 432 of tension element 406, opposite to first end 414, is coupled to a tension element break detection pulley 434, which can be implemented similarly to detection pulley 134 and pulley system 200 described above. For example, detection pulley 434 is rotatably coupled to frame 420 at an axis of rotation 436, and tension element 406 is at least partially wrapped around detection pulley 434. Detection pulley 434 is rotatable about axis 436 in a rotational range constrained by a first stop and a second stop, e.g., the detection pulley cannot rotate past the first stop in a first rotational direction about axis 436 and cannot rotate past the second stop in a second rotational direction about axis 436 that is opposite to the first rotational direction. A first torque is applied to detection pulley 434 in the first rotational direction that corresponds to a force applied to the tension element by counterbalance spring 412, and biases detection pulley 434 toward a first configuration (e.g., first orientation in this example) against the first stop. For example, the first rotational direction is in the clockwise direction as shown in FIG. 4. Examples of first and second stops are shown with respect to FIGS. 2-3.

A pulley actuator 442 is coupled between detection pulley 434 and frame 420 and applies a force (torque) to detection pulley 434 to bias detection pulley 434 in a second rotational direction about axis 436 that is opposite to the first rotational direction. For example, pulley actuator 442 can bias detection pulley 434 in the counterclockwise direction in FIG. 4, toward a second configuration (e.g., second orientation in this example) against the second stop. Actuator 442 can be any device or element that applies such a force similarly as described for FIGS. 1-3, e.g., a torsion spring.

A sensor is coupled to frame 420 to sense movement of detection pulley 434. For example, the sensor can be a pulley orientation sensor that senses rotational orientation or change in orientation of detection pulley 434. In some examples, the sensor includes rotating elements which are coupled to detection pulley 434 and can include a sensor detection element that is coupled to frame 420. In some examples, the sensor can be implemented similarly to sensor 150 of FIGS. 1-3.

In various implementations, one or more of the pulleys of the counterbalance mechanism can include grooves on their circumferential surface to support tension element 406, e.g., prevent the tension element from drifting toward the pulley edge during pulley rotation.

Other types of tension element break detection elements can be used in counterbalance mechanism 100 instead of or in addition to detection pulley 134 or 434. For example, a linear-moving detection element can be provided in a linear groove, track, or guide providing a linear degree of freedom. A tension element of the counterbalance system, e.g., similar to tension element 106, contacts or is coupled to the linear-moving detection element to apply a force that biases the detection element to stay in a first configuration. For example, the force can bias the detection element to move in a first linear direction, or stop moving in a second linear direction opposite to the first linear direction. A spring (e.g., helical spring) is coupled to the detection element that applies a linear force on the detection element in the second linear direction opposite to the first linear direction. Similarly as described for the implementations above, in standard operation, the first force is greater than the second force and causes the detection element to stay at a first configuration (e.g., a first position in this example). In some implementations, the detection element can be biased against a first stop to stay in the first configuration. In response to the tension element breaking, the second linear force is stronger than the first linear force and causes the detection element to move linearly in the second linear direction to a second configuration (e.g., a second position in this example). In some implementations, the detection element can be biased against a second stop to stay in the second configuration. A sensor system, e.g., similar to sensors described above, can detect that the detection element is at the first position or is at the second position. Some examples of a linear-moving detection element are described below with reference to FIGS. 11A and 11B.

Figure 5A:
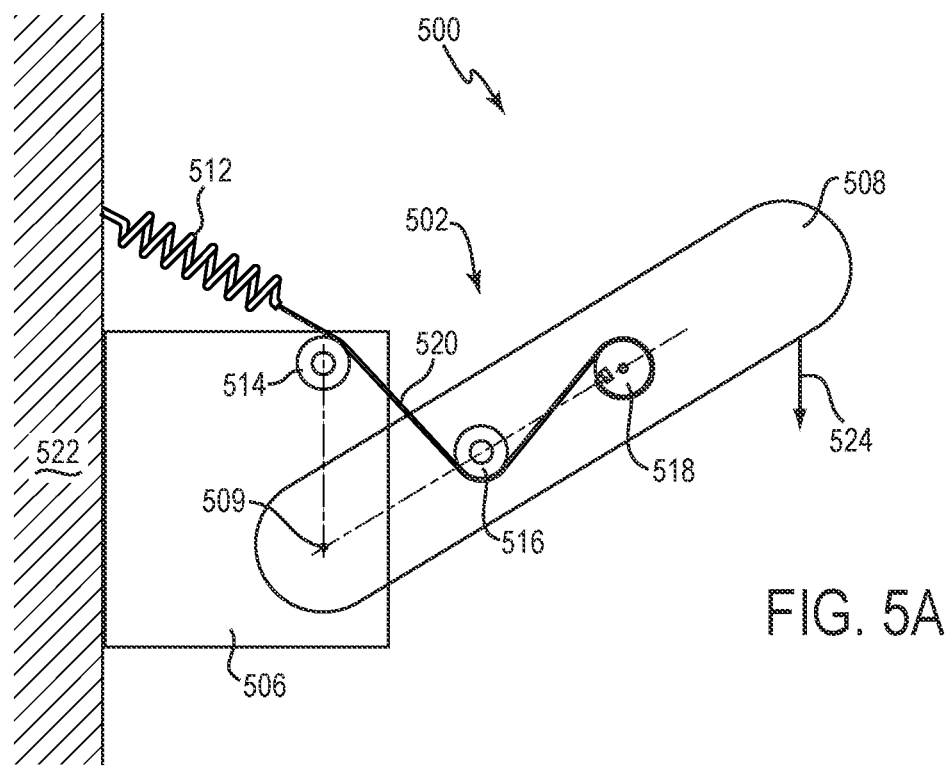
FIGS. 5A and 5B are diagrammatic illustrations of example mechanical linkages that use one or more tension element breakage detection features described herein, according to some implementations.

FIG. 5A is a diagrammatic illustration of an example mechanical linkage 500 that uses one or more tension element breakage detection features described herein, according to some implementations. Mechanical linkage 500 includes a counterbalance mechanism 502. The sizes and lengths of components and distances between components shown in FIG. 5A are not actual dimensions, but rather simplified schematic examples.

Counterbalance mechanism 502 is provided between a first member 506 and a second member 508 of the mechanical linkage, where second member 508 is rotatably coupled to first member 506 such that second member 508 rotates about axis 509 with respect to first member 506. Counterbalance mechanism 502 includes a counterbalance spring 512, a tension pulley 514, a tension pulley 516, and a detection pulley 518. First member 506 and a first end of spring 512 are coupled to a frame 522, which, for example, can be mechanically grounded or can be a portion of another member of the mechanical linkage 500. Spring 512 functions as a tension spring as shown for simplicity, but can alternatively be implemented as a compression spring as described with reference to FIG. 1. The second end of spring 512 is coupled to a cable 520 (used as the tension element). As shown, cable 520 wraps at least partially around tension pulley 514, wraps at least partially around tension pulley 516, and wraps at least partially around detection pulley 518 where it terminates. Tension pulley 514 can be rotatably coupled to first member 506, as in this example, or coupled to another member coupled to frame 522. Tension pulley 516 and detection pulley 518 are rotatably coupled to second member 508. As shown, a detection pulley can be coupled to a load for a counterbalance mechanism in some implementations.

Thus, as described above with reference to FIG. 1, spring 512 and cable 520 provide a counterbalance force on second member 508, which acts as a load, in opposition to the force of gravity being exerted on second member 508 as shown by arrow 524. Detection pulley 518 is sensed by a sensor that detects when the detection pulley 518 rotates in response to a breakage of cable 520, similarly as described above for FIGS. 1-3.

Figure 5B:
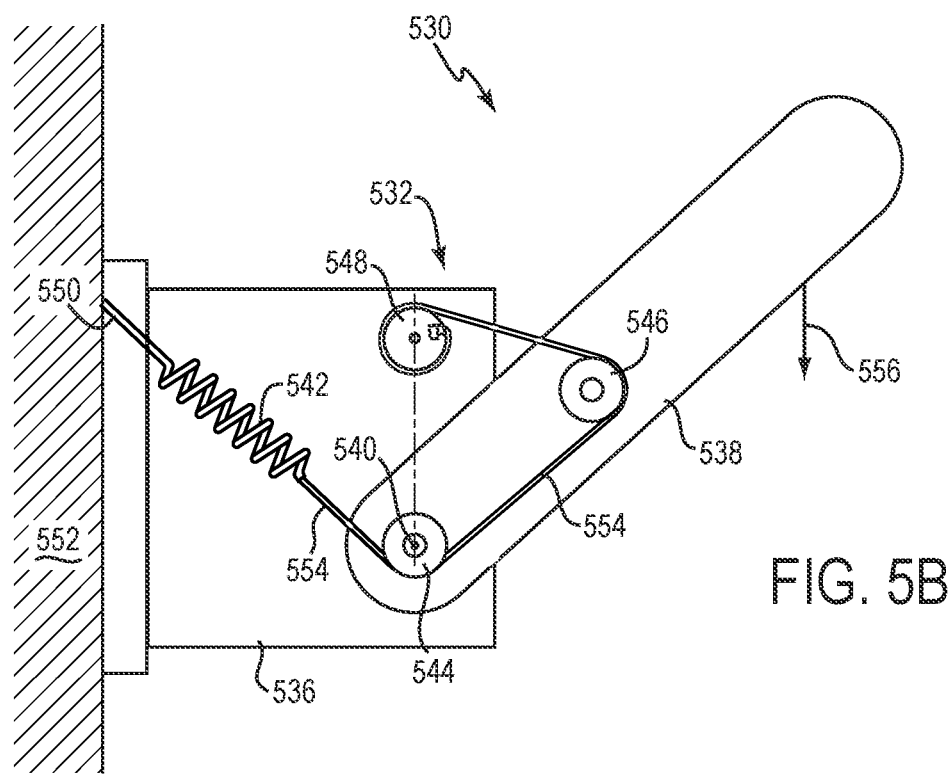

FIG. 5B is a diagrammatic illustration of another example of a mechanical linkage 530 that uses one or more tension element breakage detection features described herein, according to some implementations. Mechanical linkage 530 includes a counterbalance mechanism 532. The sizes and lengths of components and distances between components shown in FIG. 5B are not actual dimensions, but rather simplified schematic examples.

Counterbalance mechanism 532 is provided between a first member 536 and a second member 538 of the mechanical linkage, where second member 538 is rotatably coupled to first member 536 such that second member 538 rotates about axis 540 with respect to first member 536. Counterbalance mechanism 532 includes a counterbalance spring 542, a first tension pulley 544, a second tension pulley 546, and a detection pulley 548. First member 536 and a first end 550 of spring 542 is coupled to a frame 552, which, for example, can be mechanically grounded or can be a portion of another member of the mechanical linkage 530. Spring 542 functions as a tension spring as shown for simplicity, but can alternatively be implemented as a compression spring as described with reference to FIG. 1. The second end of spring 542 is coupled to a cable 554 (or other tension element). Cable 554 wraps around first tension pulley 544, wraps around second tension pulley 546, and wraps around detection pulley 548 where the cable terminates. First and second tension pulleys 544 and 546 are rotatably coupled to second member 538. Detection pulley 548 can be coupled to first member 536 or other member coupled to frame 552. Thus, a detection pulley can be rotatably coupled to the frame of a counterbalance mechanism in some implementations.

As described above with reference to FIG. 1, spring 542 and cable 554 provide a counterbalance force on second member 538, which acts as a load in opposition to the force of gravity being exerted on second member 538 as shown by arrow 556. Detection pulley 548 is sensed by a sensor that detects when the detection pulley 548 rotates in response to a breakage of cable 554, similarly as described above for FIG. 1.

Figure 6:
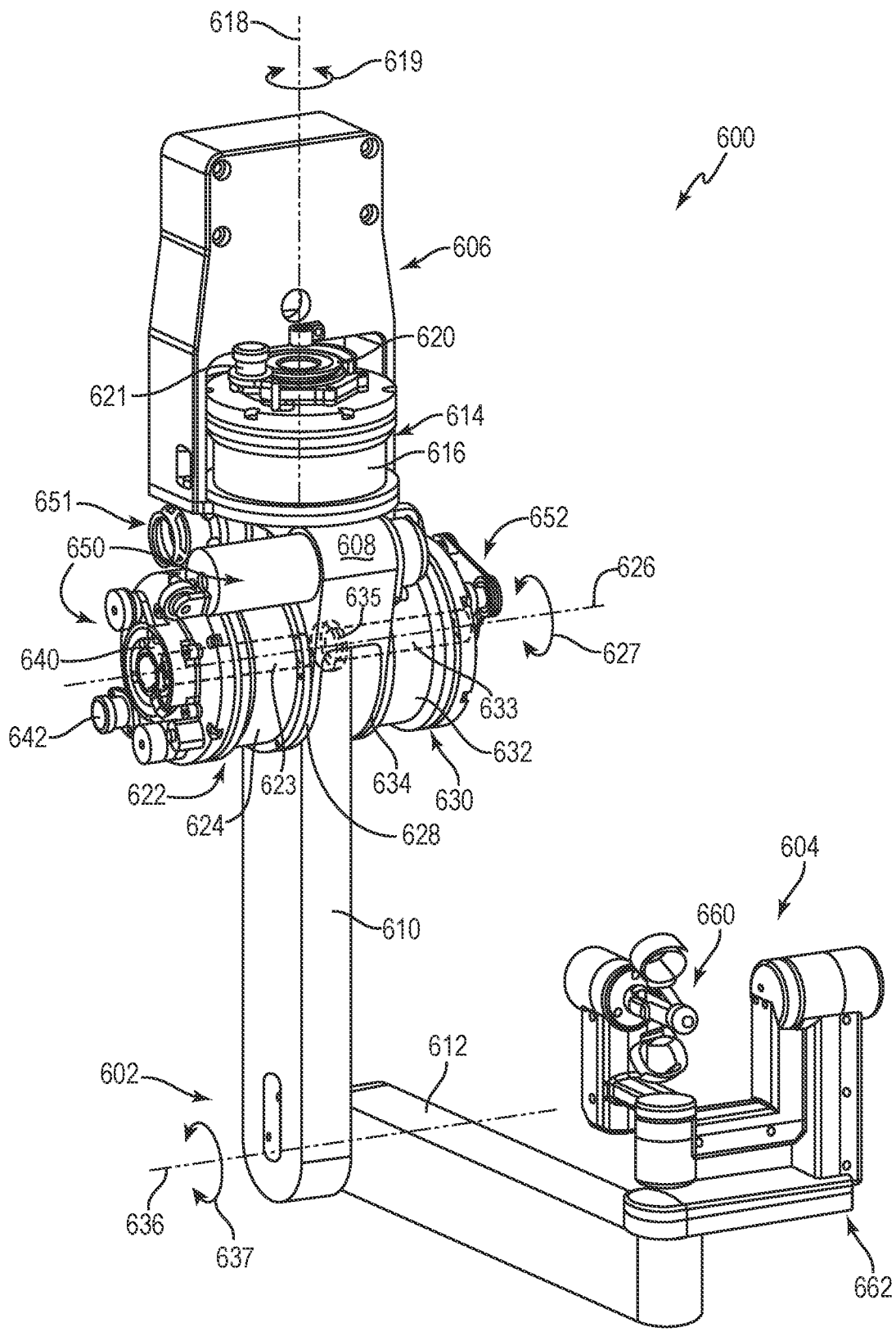
FIG. 6 is a perspective view of an example mechanical arm assembly which can include one or more tension element breakage detection features described herein, according to some implementations.

FIG. 6 is a perspective view of an example mechanical arm assembly 600 which can include one or more tension element breakage detection features described herein, according to some implementations. In some implementations, arm assembly 600 can include (or be coupled to) a control input device as described below. In some examples, arm assembly 600 can be included in a user control system (e.g., see FIG. 13 below), or can be coupled to and used in a different support frame.

Arm assembly 600 includes an arm 602 and a control input device 604. Arm 602 includes multiple linked members that are each coupled to one or more other linked members of the arm 600, thus forming a linkage. In some implementations, as shown, arm 602 includes a base member 608, a first arm member 610, and a second arm member 612. In this example, these linked members are coupled via rotary joints, where each rotary joint enables the two linked members that are coupled by that rotary joint to rotate with respect to each other.

A support 606 can be used to support the arm 602 and, in some implementations, may be considered a proximal member of the arm 602. In some implementations, support 606 is mechanically grounded. In some examples, support 606 is provided in a user control system, such as a user control system 1302 of FIG. 13. Support 606 can be connected to, or be part of, a frame or structure.

A base motor 614 is rigidly coupled to the support 606. For example, base motor 614 includes a housing 616 that is rigidly coupled to support 606. Base motor 614 includes a drive shaft that extends along an axis 618 and is rotatable about the axis 618. Base motor 614 can be controlled via signals from a control circuit to output torque on and rotate its drive shaft about axis 618. Base member 608 is rotatably coupled to support 606, e.g., at a proximal portion of base member 608, such that base member 608 is rotatable about axis 618 with respect to support 606. In some implementations, base member 608 is rigidly coupled to the drive shaft of base motor 614 such that base motor 614 can exert torque upon and rotate base member 608 about axis 618 with respect to support 606. Rotation of base member 608 about axis 618 provides a rotary degree of freedom 619, e.g., control input device 604 can be rotated in rotary degree of freedom 619 via the arm 602. In some implementations, one or more sensors, e.g., sensor 620 and/or sensor 621, can detect the rotation and/or orientation of the base member 608 about axis 618 in the rotational degree of freedom 610 and send signals describing the rotation and/or orientation to a control circuit. Such sensors can be similar to other sensors described herein (e.g., sensors 640 and 642).

A first arm motor 622 is rigidly coupled to base member 608. For example, first arm motor 622 includes a housing 624 that is rigidly coupled to base member 608. First arm motor 622 includes a drive shaft 623 that extends along and is rotatable about the axis 626. The drive shaft 623 of first arm motor 622 is directly and rigidly coupled to first arm member 610. In this example, the first arm motor housing 624 is rigidly coupled to a portion 628 of base member 608 that includes an aperture (not shown) through which drive shaft 623 of first arm motor 622 extends. First arm motor 622 can be controlled via signals from a control circuit to output torque on and rotate its drive shaft about axis 626.

A second arm motor 630 can be rigidly coupled to base member 608. For example, second arm motor 630 includes a housing 632 that is rigidly coupled to base member 608. Second arm motor 630 includes a drive shaft 633 that is rotated by second arm motor 630 about axis 626. Drive shaft 633 of second arm motor 630 is directly and rigidly coupled to a force transmission mechanism that is coupled to second arm member 612. For example, drive shaft 633 can be rigidly coupled to a first pulley 635 provided within first arm member 610. In this example, second arm motor housing 632 is rigidly coupled to a portion 634 of base member 608 that includes an aperture (not shown) through which drive shaft 633 of second arm motor 630 extends. Second arm motor 630 can be controlled via signals from a control circuit to output torque on and rotate its drive shaft 633 about axis 626.

First arm member 610 includes a proximal portion that is rotatably coupled to distal end of base member 608 by a rotary coupling, such that first arm member 610 rotates about axis 626 with respect to base member 608 at the rotary coupling. Rotation of first arm member 610 about axis 626 provides a rotary degree of freedom 627 to the control input device 604. In the described implementation, the proximal portion of first arm member 610 is rigidly coupled to drive shaft 623 of first arm motor 622 such that first arm motor 622 can exert torque upon and rotate first arm member 610 about axis 626 with respect to base member 608.

Second arm member 612 includes a proximal portion that is rotatably coupled to a distal end of first arm member 610 by a rotary coupling. Second arm member 612 can be rotated about an axis 636 at the rotary coupling with respect to first arm member 610. In some implementations, as shown, axis 636 is parallel to axis 626. Rotation of second arm member 612 about axis 636 provides a rotary degree of freedom 637 to control input device 604. In some implementations, a force transmission mechanism is provided between second arm motor 630 and second arm member 612 such that the second arm member 612 is driven by second arm motor 630 via the transmission mechanism. In some examples, the transmission mechanism can include first pulley 635 that is rigidly coupled to the drive shaft 633 of second arm motor 630, a second pulley 806 (see FIG. 8) rigidly coupled to the second arm member 612, and a tension element (see FIG. 8) connecting the first pulley 635 to the second pulley. This allows second arm motor 622 to exert torque upon and rotate second arm member 612 about axis 636 with respect to first arm member 610 and base member 608. Examples of such an implementation are described in greater detail below with respect to FIG. 8.

In some implementations, as shown in FIG. 6, first arm motor 622 and second arm motor 630 are positioned such that their drive shafts rotate about the same rotary axis 626. In some implementations, as shown in FIG. 6, motors 622 and 630 are positioned opposite to each other, e.g., on opposing sides of base member 608, such that first arm motor 622 is oriented in the opposite direction to second arm motor 630 along the rotational axis 626. In some implementations, one or more of the motors can be positioned at other locations of the arm assembly 600, and/or one or more motors can be omitted. In some implementations, a respective gearing mechanism can be coupled between any one or more of the motors 614, 622 and 630 and their driven members instead of the direct coupling of motor shafts to driven members shown in FIG. 6, e.g., to increase the amplitude of force output from the motors. For example, such a gearing mechanism can include a capstan drive mechanism, rotary gears or pulleys, and/or other mechanism.

In some implementations, one or more sensors can detect the rotation and/or orientation of first arm member 610 about axis 626 and send signals describing the rotation and/or orientation to a control circuit. For example, a sensor 640 can be coupled to the first arm motor 622 to detect rotation of drive shaft 623 of first arm motor 622 about axis 626, and thus detect rotation of first arm member 610 about axis 626. In some examples, sensor 640 can include a rotary encoder or other type of sensor that is coupled to drive shaft 623 and senses the rotation of the drive shaft. In another example, a sensor 642 can be coupled to and sense rotation of drive shaft 623 of the first arm motor 622 about axis 626, and thus detect rotation of first arm member 610 about axis 626. Some examples are described with reference to FIG. 7.

In some implementations, one or more counterbalance mechanisms are coupled to arm 602 to exert forces, for example, on first arm member 610 in opposition to the force of gravity. For example, a first counterbalance mechanism 650 can be used to apply a first counterbalance force to first arm member 610 and a second counterbalance mechanism 652 can be used to apply a second counterbalance force to second arm member 612. Example counterbalance mechanisms that can be used for counterbalance mechanism 650 are described in greater detail below with respect to FIG. 7.

Control input device 604 is coupled to a second (e.g., distal) portion of second arm member 612. In some implementations, control input device 604 is rotatably coupled to second arm member 612. In other implementations, control input device 604 can be coupled in other ways, e.g., rigidly coupled or translatably coupled to second arm member 612. Control input device 604 shown in FIG. 6 is one example of an input device that can be coupled to a distal end of arm 602. In this example, control input device 604 includes a handle 660 that is grasped by a user, e.g., by fingers of a hand of the user. Arm 602 provides multiple degrees of freedom to handle 660 based on the rotary joints of the arm described above, e.g., rotation of links of arm 602 about axes 618, 626, and 636. In some implementations, as in the example shown in FIG. 6, control input device 604 provides degrees of freedom to handle 660 which are in addition to the degrees of freedom provided to handle 660 by the arm 602. For example, a gimbal mechanism 662 or other linkage can couple handle 660 to second arm member 612, where each link is rotatably coupled to one or more other links in the gimbal mechanism.

Figure 7:
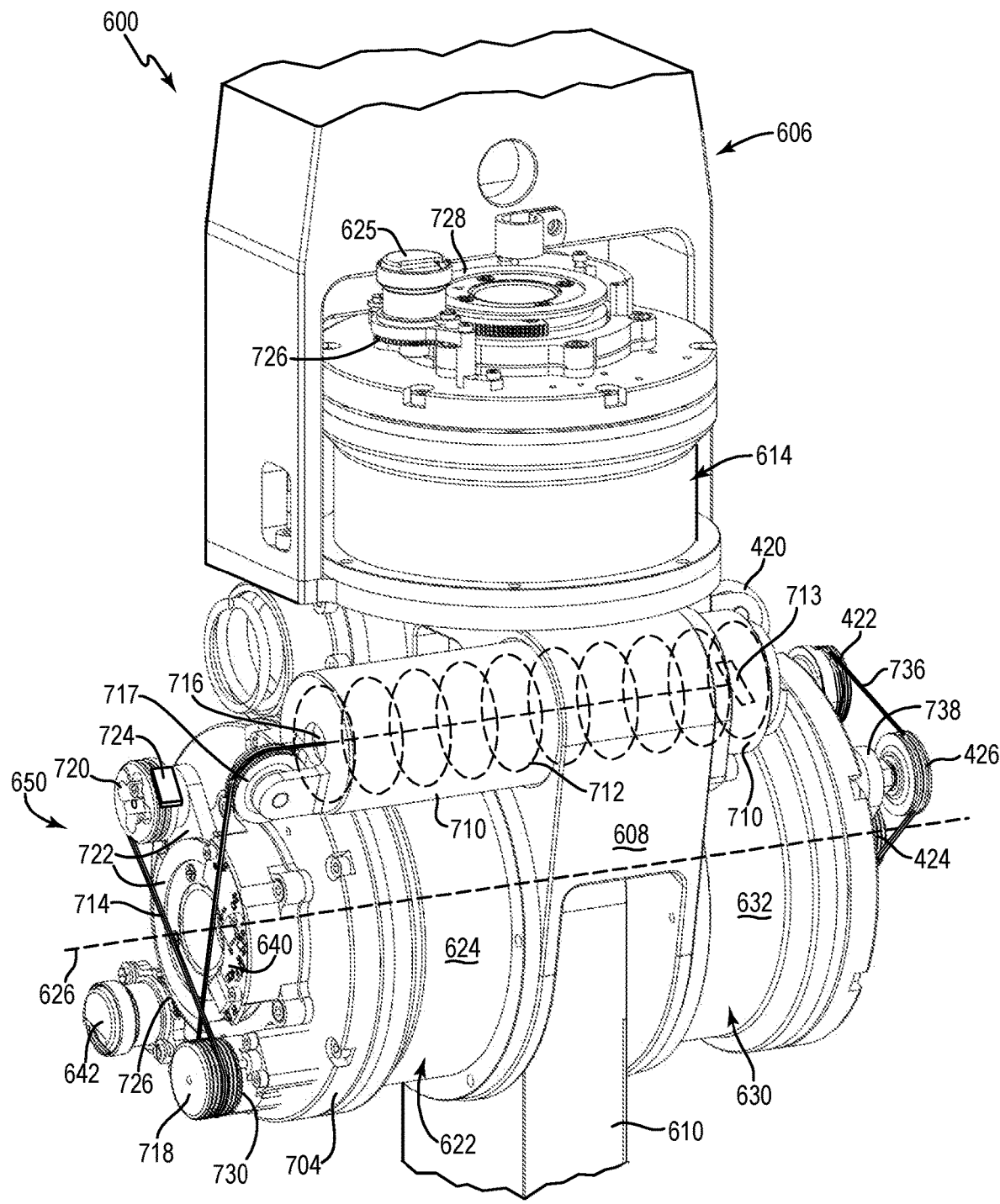
FIG. 7 is a perspective view of a portion of the arm assembly of FIG. 6, according to some implementations.

FIG. 7 is a perspective view of a portion of the arm assembly 600 of FIG. 6, including support 606, base member 608, and a portion of first arm member 610. Counterbalance mechanism 650 is shown in greater detail according to some implementations.

Counterbalance mechanism 650 provides forces opposing gravitational forces on the first arm member 610 of arm assembly 600, e.g., allowing reduced force magnitudes to be output from first arm motor 622 to move or support the first arm member 610 against gravity as compared to a similar mechanical arm assembly that does not use such a counterbalance mechanism. In some implementations, counterbalance mechanism 650 includes a spring housing 710 that houses a spring 712 and is coupled to base member 608. A cable 714 (which is shown doubled in FIG. 7, e.g., a single cable that is doubled, or two cables) is coupled to the spring 712 by an element 713 that attaches the end of cable 714 to the spring 712. Cable 714 is routed out of an opening 716 of spring housing 710 and around a pulley 717 coupled to spring housing 710. Cable 714 is further routed around a pulley 718 that is rotatably coupled to housing 624 of first arm motor 622. Cable 714 is terminated at a detection pulley 720 that is rotatably coupled to a rotating portion 722 of the first arm motor 622. Rotating portion 722 is rigidly coupled to rotating drive shaft 623 of first arm motor 622. Rotating portion 722 thus rotates about axis 626 concurrently with the rotation of drive shaft 623 and first arm member 610. In some examples, as shown, detection pulley 720 can be coupled to rotating portion 722 such that the axis of rotation of detection pulley 720 is at a location offset from axis of rotation 626 of rotating drive shaft 623.

Detection pulley 720 is used to detect a break in cable 714 similarly as described above for FIGS. 1-5B. In the shown configuration, cable 714 is intact (unbroken) and detection pulley 720 is in a first rotational position due to the force provided by cable 714 on detection pulley 720. After a break of cable 714, detection pulley 714 rotates to a second rotational position. In some implementations, as shown, detection pulley sensor 724 can be positioned near or adjacent to detection pulley 720 and can be any of the sensors described above with respect to FIGS. 1-4. Some examples of detection pulley 720 and its operation are described below with reference to FIG. 10.

Counterbalance mechanism 650 provides counterbalance forces on the rotation of first arm member 610 about axis 626. For example, as first arm member 610 rotates in either direction about axis 626, the rotating portion 722 rotates, which causes cable 714 to pull on the spring 712. Spring 712 resists this pull, providing a counterbalance force to the rotation of first arm member 610 about axis 626. Other types or configurations of counterbalance mechanisms can be used in other implementations.

In some implementations, sensor 642 can be, for example, a rotary encoder or other type of sensor, and is coupled to a rotating gear 726 that engages a toothed edge of the rotating portion 722. The rotation of rotating portion 722, coinciding with the rotation of drive shaft 623 of the first arm motor 622, is sensed by sensor 642 via the rotating gear 726.

In some implementations, a sensor 730, such as a rotary encoder or other type of sensor, can be coupled to pulley 718 and sense the rotation of pulley 718 with respect to housing 624 of first arm motor 622 when cable 714 rotates the pulley 718. Pulley 718 rotates in conjunction with rotation of first arm member 610, such that sensor 730 can sense rotation of first arm member 610 via sensing rotation of pulley 718. For example, sensor 730 can be a backup tension element break detection sensor that senses cable motion via pulley 718. The sensed cable motion can be compared and correlated with motion of first arm member 610 as detected by one or more other sensors (e.g., sensors 640 and/or 642), such that if the motion of pulley 718 and first arm member 610 does not match, a tension element break may be detected.

In some implementations, the axes of rotation or center points of pulleys 718 and 720 (e.g., points in the center of the pulleys that intersect the axes of rotation of the pulleys) can be adjusted to change counterbalance mechanism parameters. For example, changing the distance from axis 626 to the center point of pulley 720, and/or changing the distance from axis 626 to the center point of pulley 718, will adjust properties of counterbalance mechanism 650 to provide variations in counterbalance force magnitude for the amount of weight of the load being balanced. Adjusting the length of the tension element (e.g., cable 714) and/or the spring rate of spring 712 also changes counterbalance mechanism properties.

Figure 8:
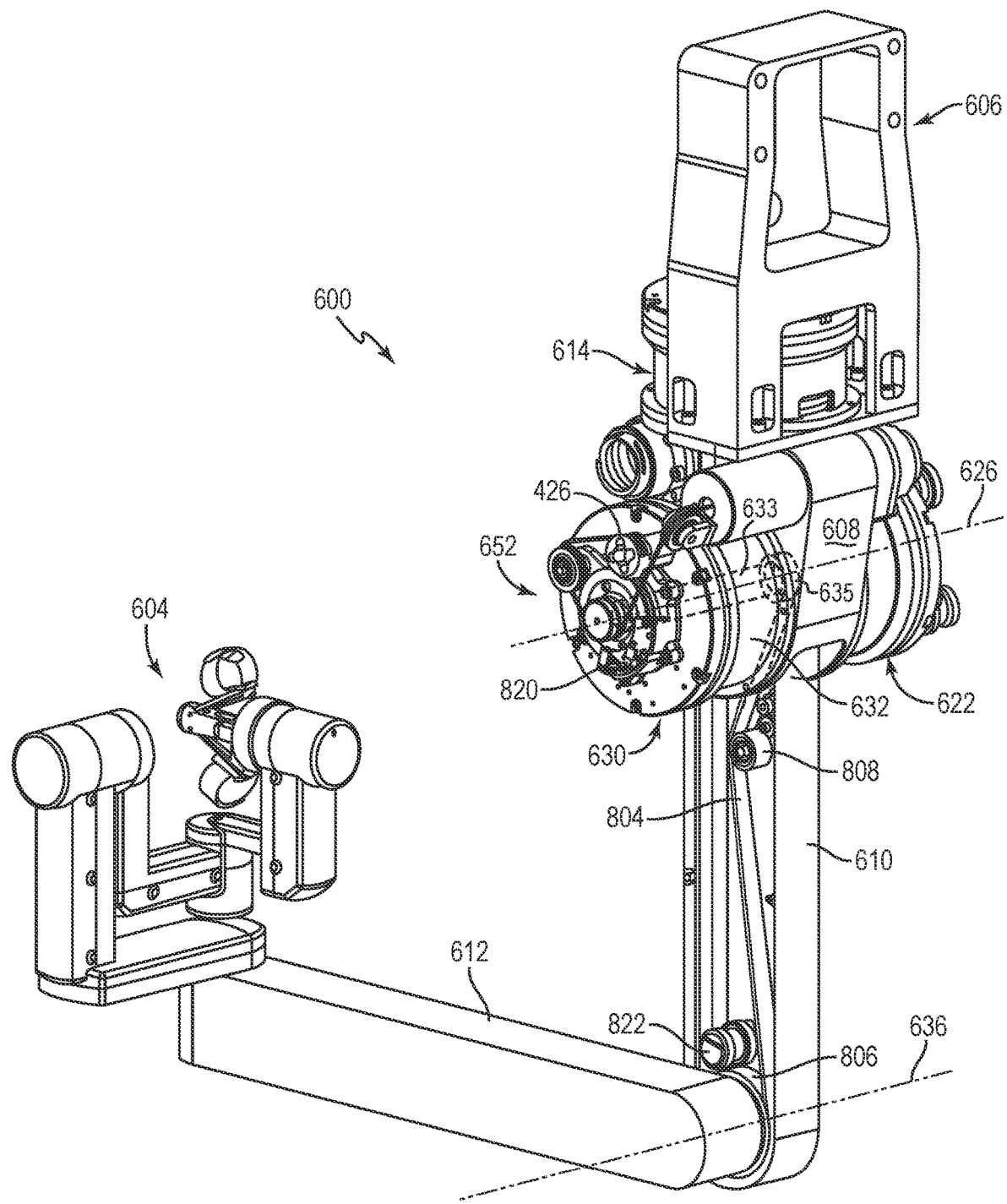
FIG. 8 is another perspective view of an arm of the arm assembly of FIG. 6, according to some implementations.

FIG. 8 is another perspective view of arm 602 of arm assembly 600 of FIG. 6, where arm 602 is shown with a portion of the interior of first arm member 610 exposed.

In this example, a pulley transmission mechanism is provided in first arm member 610 as a force transmission mechanism coupling second arm motor 630 to second arm member 612. As shown, second arm member 612 includes a tension element, e.g., a belt 804, coupled to (wrapped around) first pulley 635 that is positioned within the proximal portion of first arm member 610. First pulley 635 is rigidly coupled to drive shaft 633 of second arm motor 630. For example, belt 804 can be made of stainless steel or other material of suitable strength, or can be a cable, rope, chain, or other type of tension element. Belt 804 extends along the length and in the interior of first arm member 610 to the distal portion of first arm member 610, where belt 804 is wrapped around a second pulley 806. Second pulley 806 is rotatably coupled to the distal portion of first arm member 610 and is rigidly coupled to the proximal portion of second arm member 612. Second pulley 806 is caused to rotate about axis 636 by the moving of belt 804. In some implementations, belt 804 can be at least partially wrapped around one or more rollers, e.g., roller 808, to provide tension on belt 804.

The force transmission mechanism, including first pulley 635, belt 804, and second pulley 806, transmits rotational forces from second arm motor 630 to second arm member 612. For example, second arm motor 630 is controlled to rotate the first pulley, which causes belt 804 to move and causes second pulley 806 to rotate. The rotation of second pulley 806 exerts torque on, and/or causes rotation of, second arm member 612 about axis 636.

In other implementations, a different type of force transmission mechanism can be used instead of the pulley transmission mechanism shown in FIG. 8. For example, a rigid member can be rotatably coupled to the first pulley 635 (or a driven plate similar to a pulley), or can be rotatably coupled to drive shaft 633 of the second arm motor, at a location offset from axis 626. The rigid member extends parallel to first arm member 610 and is rotatably coupled to second arm member 612 at a location offset from axis 636. In some examples, the rigid member, first arm member 610, and lines drawn between the rotary couplings of the rigid member and first arm member 610 can form a parallelogram. As first pulley 635 rotates, the rigid member is moved away from and toward second arm member 612, which moves second arm member 612 about axis 636 with respect to first arm member 610 in corresponding directions.

In some implementations, one or more sensors can detect the rotation and/or orientation of second arm member 612 about axis 636 and send signals describing the rotation and/or orientation to a control circuit. For example, a sensor 820 can be coupled to second arm motor 630 to detect rotation of drive shaft 633 of second arm motor 630 about axis 626, and thus detect rotation of first pulley 635 about axis 626 due to corresponding rotation of second arm member 612 about axis 636. In some examples, sensor 820 can include a rotary encoder or other type of sensor that is coupled to drive shaft 633 and senses the rotation of the drive shaft, thereby sensing corresponding rotation of second arm member 612.

In another example, a sensor 822 can be coupled to and sense rotation of second pulley 806, thus detecting corresponding rotation of second arm member 612 that is coupled to second pulley 806. For example, sensor 822 can include a rotary encoder or other type of sensor, that is coupled to a gear that engages a toothed edge of second pulley 806. The gear of the sensor rotates in conjunction with second pulley 806 (e.g., the sensor gear engages with a sector gear mounted to pulley 806), allowing the sensor 822 to sense the rotation of the second pulley 806. Other types of sensors can also or alternatively be used.

In some implementations, one or more counterbalance mechanisms are coupled to arm 602 to exert forces, for example, on second arm member 612 in opposition to the force of gravity. For example, second counterbalance mechanism 652 can be used to apply a second counterbalance force to second arm member 612. Example counterbalance mechanisms that can be used for counterbalance mechanism 652 are described in greater detail below with respect to FIG. 9.

Figure 9:
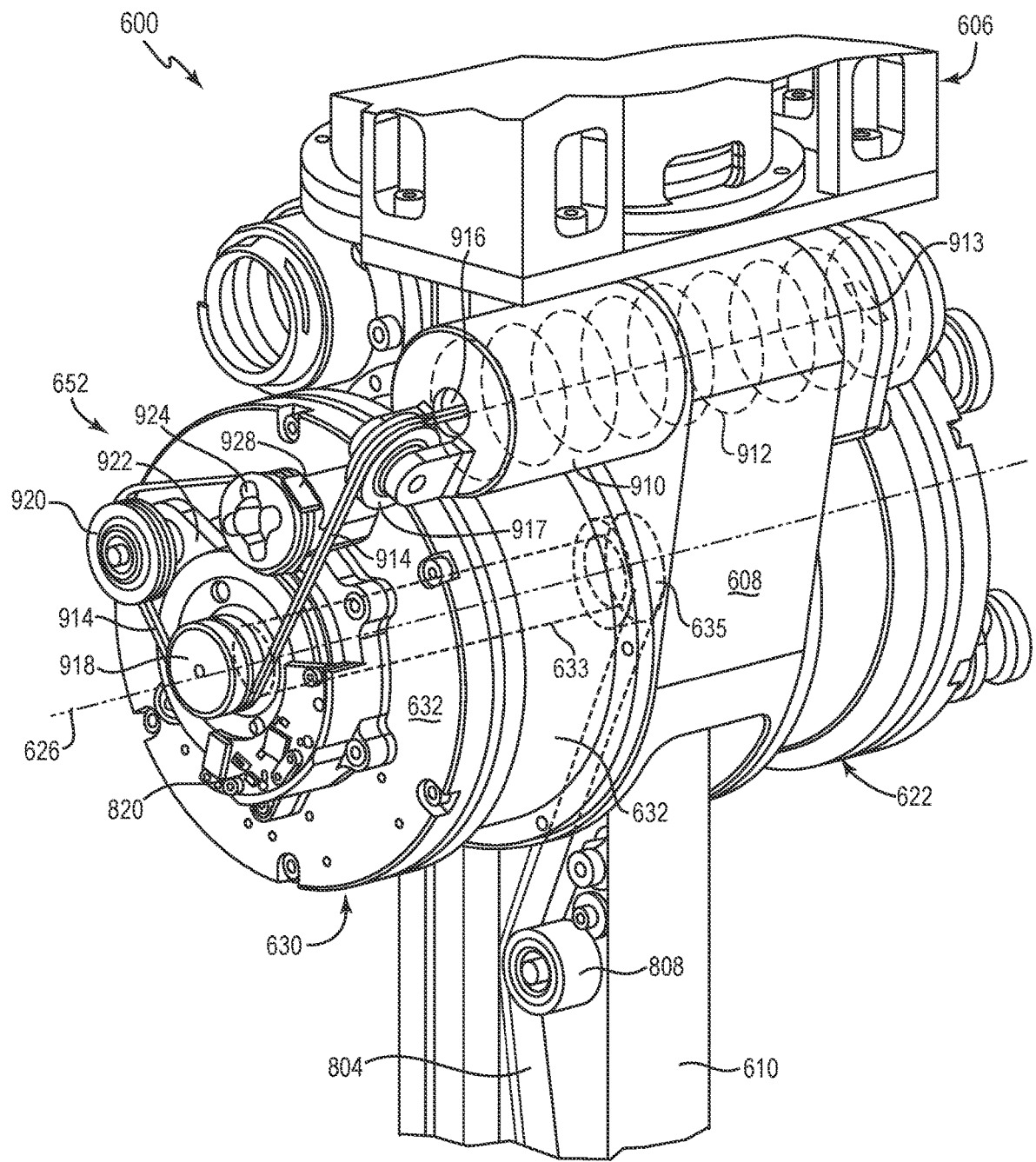
FIG. 9 is another perspective view of a portion of the arm assembly of FIG. 6, according to some implementations.

FIG. 9 is another perspective view of a portion of the arm assembly 600 of FIG. 6, including support 606, base member 608, and a portion of first arm member 610. Counterbalance mechanism 652 is shown in greater detail according to some implementations.

Counterbalance mechanism 652 provides forces opposing gravitational forces on second arm member 612 of arm assembly 600 (see FIG. 8), e.g., allowing reduced force magnitudes to be output from second arm motor 630 to move or support the second arm member 612 against gravity as compared to a similar mechanical arm assembly that does not use a counterbalance mechanism. In some implementations, counterbalance mechanism 652 includes a spring housing 910 that houses a spring 912 and is coupled to base member 608. A cable 914 (which is shown doubled in FIG. 9, e.g., a single cable that is doubled, or two cables) is coupled to spring 912 by an element 913 that attaches the end of cable 914 to spring 912. Cable 914 is routed out of an opening 916 of spring housing 910 and around a pulley 917 coupled to spring housing 910. Cable 914 is further routed around a pulley 918 that is rotatably coupled to drive shaft 633 of second arm motor 630. Cable 914 is then routed around a pulley 920 that is rigidly coupled to a rotating portion 922 of second arm motor 630. Rotating portion 922 is rigidly coupled to rotating drive shaft 633 of second arm motor 630. Rotating portion 922 thus rotates about axis 626 concurrently with the rotation of drive shaft 633 and first pulley 635. In some examples, as shown, pulley 920 can be coupled to rotating portion 922 such that the center of pulley 920 is at a location offset from axis of rotation 626 of rotating drive shaft 633.

Cable 914 is terminated at a detection pulley 924 that is rotatably coupled to housing 632 of second arm motor 630. Detection pulley 924 is used to detect a break in cable 914. In the shown configuration, cable 914 is intact (unbroken) and detection pulley 924 is in a first rotational position due to the force provided by cable 914 on detection pulley 924. After a break of cable 914, detection pulley 924 rotates to a second rotational position. In some implementations, as shown, detection pulley sensor 928 can be positioned near or adjacent to the detection pulley 924 and can be any of the sensors described above with respect to FIGS. 1-4. Some examples of detection pulley 924 and its operation are described below with reference to FIG. 10.

Counterbalance mechanism 652 provides counterbalance forces on the rotation of second arm member 612 about axis 636. For example, as second arm member 612 rotates in either direction about axis 636, the first pulley 635, drive shaft 633, and rotating portion 922 rotate, which causes cable 914 to pull on spring 912. Spring 912 resists this pull, providing a counterbalance force to the rotation of second arm member 612 about axis 636 via first pulley 635, belt 804, and second pulley 806. Other types or configurations of counterbalance mechanisms can be used in other implementations.

In some implementations, a sensor (not shown), such as a rotary encoder or other type of sensor, can be coupled to pulley 918 and sense the rotation of pulley 918 with respect to housing 632 of second arm motor 630 when cable 914 rotates the pulley 918. Pulley 918 rotates in conjunction with rotation of second arm member 612, such that the sensor can sense rotation of second arm member 612 via sensing rotation of pulley 918. For example, such a sensor can be a backup tension element break detection sensor that senses cable motion via pulley 918. The sensed cable motion can be compared and correlated with motion of second arm member 612 as detected by one or more other sensors (e.g., sensors 820 and/or 822), such that if the motion of pulley 918 and second arm member 612 does not match, a cable break may be detected.

In some implementations, the axes of rotation or center points of pulleys 918, 920, and 924 (e.g., points in the center of the pulleys that intersect the axes of rotation of the pulleys) can be the corners or vertices of a triangle configuration, and can be adjusted to change counterbalance mechanism parameters. For example, changing the distance of one of the sides of the triangle adjusts the counterbalance mechanism provides variations in counterbalance force magnitude for the weight of the load being balanced. Adjusting the length of the tension element (e.g., cable 914) and/or the spring rate of spring 912 also changes counterbalance mechanism properties.

Figure 10:
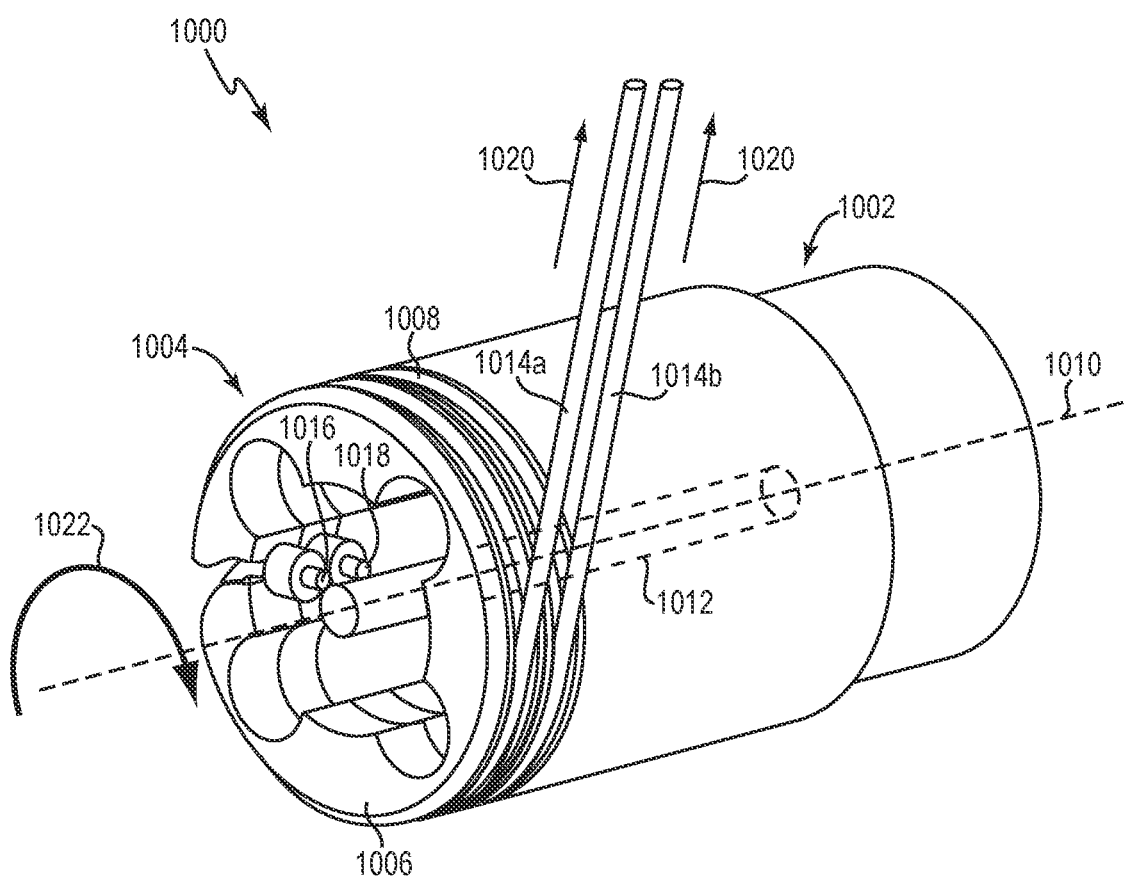
FIG. 10 is a diagrammatic illustration of an example tension element breakage detection pulley, according to some implementations.

FIG. 10 is a diagrammatic illustration of an example tension element break detection mechanism, shown as detection pulley 1000, according to some implementations, that can be used in one or more implementations described herein. For example, detection pulley 1000 can be detection pulley 134, 434, 518, 548, 720, or 924 as described above in various implementations.

Detection pulley 1000 includes a support portion 1002 and a rotating pulley portion 1004. Support portion 1002 is rigidly coupled to a frame, support, or surface. For example, support portion 1002 can be rigidly coupled to load 130, frame 420, second member 508 or 538, rotating portion 722 of first arm motor 622, or housing 632 of second arm motor 630.

Rotating pulley portion 1004 is rotatably coupled to support portion 1002. Rotating pulley portion 1004 includes a first pulley 1006 and a second pulley 1008 that each can rotate about an axis 1010. In this example, first pulley 1006 is rotatably coupled to a shaft 1012 extending through the center of rotating pulley portion 1004. Second pulley 1008 is also rotatably coupled to shaft 1012. First pulley 1006 is rotatable about axis 1010 independently of the rotation of second pulley 1008 about axis 1010.

A cable 1014 (or other tension element) is wrapped around the first pulley 1006 and second pulley 1008 and terminates at these pulleys 1006 and 1008. In this example, cable 1014 is a single cable in which both ends of the cable terminate at rotating pulley portion 1004, and cable 1014 includes cable portions 1014a and 1014b. In other implementations, cable 1014 can be two separate cables. Cable portion 1014a is wrapped around first pulley 1006 (e.g., within a groove in the circumferential surface of first pulley 1006) and has an end 1016 that extends through an aperture in first pulley 1006 to secure the end 1016 in place at the first pulley 1006. Cable portion 1014b is wrapped around second pulley 1008 (e.g., within a groove in the circumferential surface of second pulley 1008) and has an end 1018 that extends through an aperture in second pulley 1008 to secure the end 1018 in place at the second pulley 1008. Cable 1014 can be wrapped around various other elements of a counterbalance mechanism between its ends 1016 and 1018, some examples of which are described in implementations herein.

In operation of a counterbalance mechanism including detection pulley 1000, first pulley 1006 and second pulley 1008 are in a rotational orientation as shown, e.g., when tension is provided on cable 1014 in a direction as shown by arrows 1020. Tension 1020 provides a torque on first pulley 1006 and second pulley 1008 to rotate these pulleys about axis 1010 in one direction. That torque has a higher magnitude than opposing torque provided by a pulley actuator coupled to the pulleys 1006 and 1008, such as a torsion spring that biases the pulleys in the opposite direction 1022 (e.g., as described above). Thus, pulleys 1006 and 1008 are oriented against a first stop (examples of which are described above) in the shown position.

If cable 1014 breaks (e.g., a portion of cable 1014 that includes cable portion 1014a or 1014b is broken), then the torque caused by tension 1020 is removed or reduced below the magnitude of the torque provided by the pulley actuator, and first pulley 1006 and second pulley 1008 are rotated in the direction 1022 until they are oriented against a second stop.

The change in position is detected by one or more sensors, e.g., similarly as described above with respect to FIGS. 2 and 3. For example, a first sensor can be coupled to first pulley 1006 and can detect multiple orientations, and/or changes in orientation, of first pulley 1006, and a second sensor can be coupled to second pulley 1008 and can detect multiple orientations, or changes in orientation, of second pulley 1008 independently of first pulley 1006 and the first sensor. In some examples, a first sensor element can be coupled to first pulley 1006, a second sensor element is coupled to support portion 1002 (or other element) that can detect orientations of the first sensor element, a third sensor element can be coupled to second pulley 1008, and a fourth sensor element is coupled to support portion 1002 (or other element) that can detect orientations of the third sensor element. In other implementations, a single sensor or sensor element can be used to detect multiple orientations, and/or changes in orientation, of first pulley 1006 and/or second pulley 1008. For example, each of first pulley 1006 and second pulley 1008 can have a sensor element coupled thereto, and a single sensor element (e.g., a detector) can be coupled to support portion 1002 to detect the orientation and/or change in orientation of either sensor element coupled to first pulley 1006 and second pulley 1008.

Figure 11A:
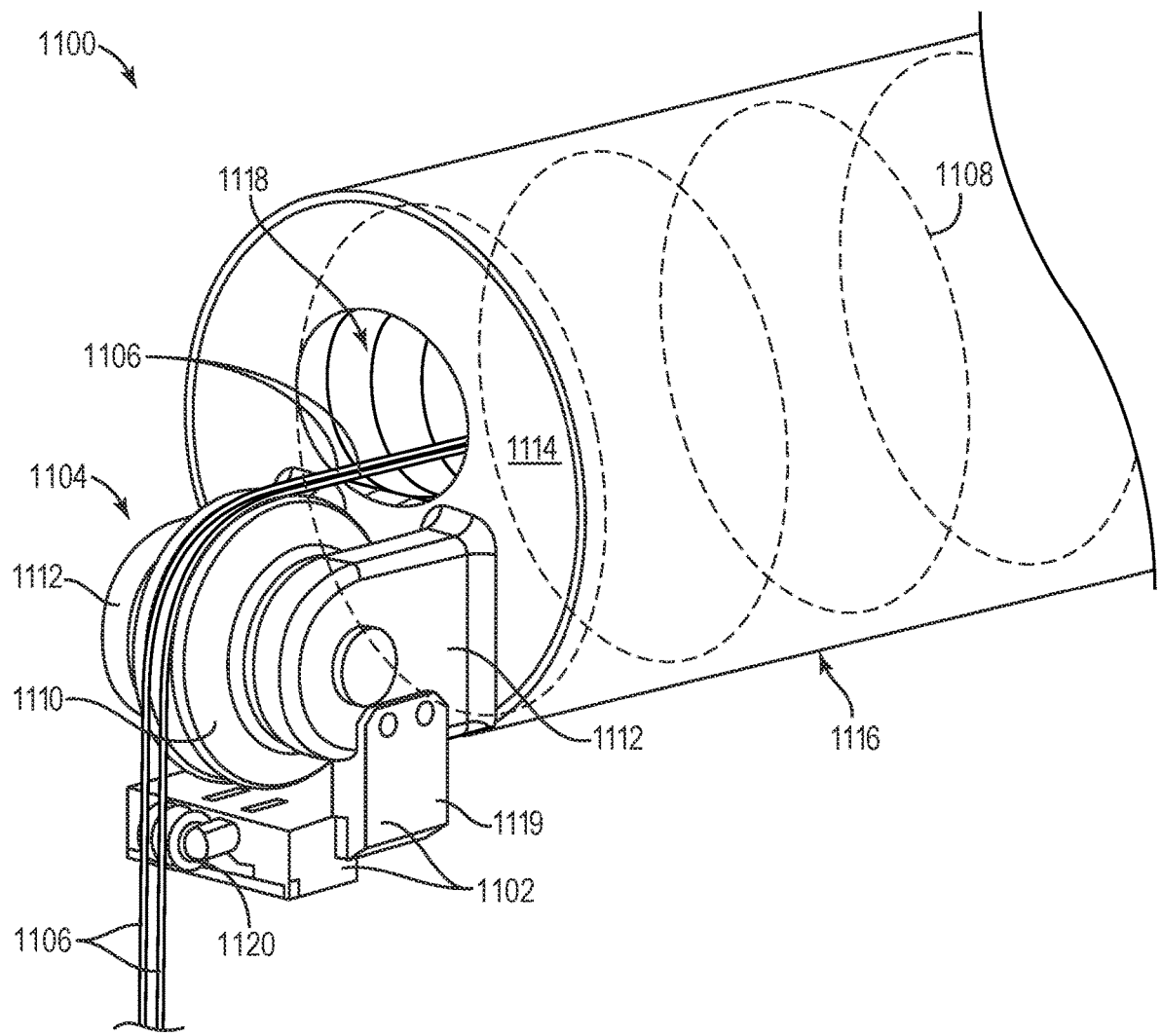
FIGS. 11A and 11B are perspective views of another example of a tension element breakage detection mechanism, according to some implementation.

FIG. 11A is a perspective view of another example of a tension element break detection device 1100, according to some implementations, that can be used in one or more implementations described herein. In some examples, tension element break detection device 1100 can be used in arm assembly 600 of FIG. 6 or in other mechanical systems having a counterbalance system, e.g., replacing or in addition to the implementations of tension element break detection mechanisms described above with respect to FIGS. 6-10.

Tension element break detection device 1100 includes a detection device housing 1102 that is coupled to a component of a counterbalance mechanism or mechanical system such that the housing 1102 is positioned near a tension element (e.g., cable) being monitored for breakage. In the example shown in FIG. 11A, device housing 1102 is coupled to a pulley mechanism 1104 that routes a tension element (e.g., cable 1106) from a counterbalance spring 1108 to other members of a mechanical system. Pulley mechanism 1104 includes a pulley 1110 rotatably coupled to a pulley support 1112. In this example, pulley support 1112 includes two parallel supports that are coupled to a surface 1114 of a spring housing 1116 that houses counterbalance spring 1108. Pulley 1110 is rotatably coupled between the parallel supports. For example, cable 1106 can be routed from counterbalance spring 1108, through an aperture 1118 in spring housing 1116, and at least partially around pulley 1110.

Cable 1106 is shown as a doubled cable, but can be a single cable or two cables in other implementations. In some examples, spring housing 1116 can be similar to spring housing 710, pulley 1110 can be similar to pulley 717, and counterbalance spring 1108 can be similar to counterbalance spring 712 described above with reference to FIG. 7. In further examples, spring housing 1116 can be similar to spring housing 910, pulley 1110 can be similar to pulley 917, and counterbalance spring 1108 can be similar to counterbalance spring 912 described above with reference to FIG. 9.

In some implementations, as shown, device housing 1102 of tension element break detection device 1100 can be coupled to pulley support 1112. For example, device housing 1102 can be coupled on one side of pulley support 1112 that is opposite to aperture 1118 in spring housing 1116. In the example shown, device housing 1102 is coupled to pulley support 1112 by members 1119 on either side of device housing 1102.

Device housing 1102 includes one or more detection elements that can include detection pulleys 1120 that contact the cable 1106 during normal operation of the counterbalance system, e.g., while the cable 1106 is in an unbroken state. The detection elements that include pulleys 1120 are linearly moved in response to breakage of cable 1106, which is detected by the detection device 1100 as described in greater detail with respect to FIG. 11B.

In other implementations, device housing 1102 can be coupled to other locations of a mechanical system or counterbalance mechanism, e.g., locations of the system at which the detection pulleys 1120 can contact cable 1106. For example, device housing 1102 can be coupled to spring housing 1116, or a portion of a member of mechanical arm that is near the cable 1106 (e.g., on a mechanical arm of an assembly similar to arm assembly 600 of FIG. 6, or other mechanical system).

In some examples, tension element break detection device 1100 can be used in arm assembly 600 of FIG. 6, e.g., instead of detection pulley 720. Detection device 1100 can also or alternatively be used in arm assembly 600 of FIG. 9, e.g., instead of detection pulley 924. For example, detection pulley 720 and/or detection pulley 924 can be replaced by standard fixed pulley(s) in these implementations. In some implementations, detection device 1100 can be used in arm assembly 600 of FIG. 6 in addition to using detection pulley 720 and/or detection pulley 924 in the arm assembly 600.

Figure 11B:
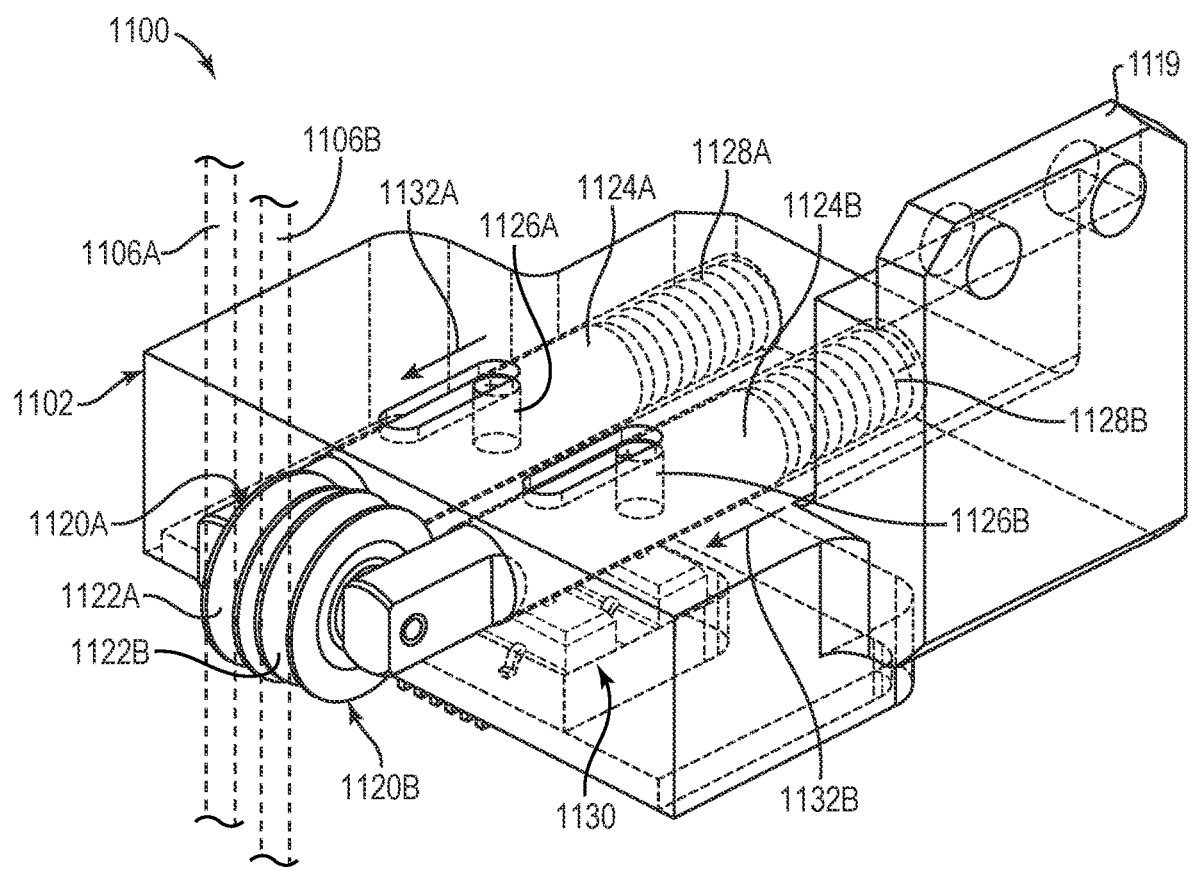

FIG. 11B is a perspective view of example components of tension element break detection device 1100 of FIG. 11A. Device housing 1102 can be coupled to a component of the counterbalance system and/or mechanical system that is being counterbalanced, as described above for FIG. 11A.

Device housing 1102 includes one or more detection elements that include one or more detection pulleys 1120 as described with reference to FIG. 11A. In this example, two detection elements are used and include a detection pulley 1120A and a detection pulley 1120B. In this example, a cable 1106A is routed partially around detection pulley 1120A, e.g., through a groove 1122A in detection pulley 1120A. Cable 1106B can be routed partially around detection pulley 1120B, e.g., through a groove 1122B in detection pulley 1120B. Cable 1106A and cable 1106B can be portions of a single cable that is doubled, as described with reference to FIG. 11A, or can be separate (disconnected) cables. In some implementations, a single cable 1106 can be used, which is wrapped partially around a single detection pulley 1120.

Detection pulley 1120A is coupled to a linear member such as a plunger 1124A that extends within device housing 1102. For example, the detection pulley 1120A and plunger 1124A can form a detection element. Plunger 1124A can be moved linearly (translate) along its long axis within a channel in device housing 1102 in a linear degree of freedom. A spring 1128A is coupled to the second end of plunger 1124A that is opposite to the first end of plunger 1124A coupled to detection pulley 1120A. For example, spring 1128A can be a helical spring that applies a linear force to plunger 1124A.

In some implementations, a magnet 1126A is included in or coupled to plunger 1124A, e.g., between detection pulley 1120A and spring 1128A. The magnet 1126A is sensed by a magnetic sensor 1130, e.g., a Hall effect sensor. Magnetic sensor 1130 can, for example, sense a position of the magnet 1126A, or a change of position of the magnet, in the linear degree of freedom of the detection element including plunger 1124A. For example, magnetic sensor 1130 can act as a magnetic field sensing switch that detects when magnet 1126A moves to or past a threshold position in the linear degree of freedom of plunger 1124A, and outputs a signal indicating that the threshold position of the magnet 1126A has been sensed.

Detection pulley 1120B can be included in device housing 1102 similarly to detection pulley 1120A. Detection pulley 1120B is coupled to a plunger 1124B that extends into device housing 1102. For example, the detection pulley 1120B and plunger 1124B can form a second detection element. Plunger 1124B can be moved linearly (translate) along its long axis within a groove in device housing 1102 in a linear degree of freedom. A spring 1128B is fixed to the second end of plunger 1124B that is opposite to the first end of plunger 1124B coupled to detection pulley 1120B. For example, spring 1128B can be a helical spring that applies a linear force to plunger 1124B. A magnet 1126B is included in or coupled to plunger 1124B, e.g., between detection pulley 1120B and spring 1128B. The magnet 1126B is sensed by a magnetic sensor 1130. Magnetic sensor 1130 can, for example, sense a position of magnet 1126B (or a change of position of the magnet) in the linear degree of freedom of plunger 1124B. For example, magnetic sensor 1130 can act as a magnetic field sensing switch that detects when magnet 1126B moves to or past a threshold position in the linear degree of freedom of plunger 1124B. Magnetic sensor 1130 outputs a signal indicating that the threshold position of the magnet 1126B has been sensed.

In operation of a counterbalance system with an intact cable (and without slack in the cable), detection pulley 1120A is pushed against cable 1106A in a direction indicated by arrow 1132A, due to plunger 1124A being forced by spring 1128A in that direction. Thus, cable 1106A provides an opposing force in opposition to the force on the detection element applied by spring 1128A, e.g., cable 1106A biases the detection element including pulley 1120A and plunger 1124A in the opposite direction to a direction 1132A. This results in a first configuration (first position) of the detection element including pulley 1120A and plunger 1124A while the cable 1106A is unbroken and/or without slack. Detection pulley 1120A rotates as cable 1106A moves. Similarly, cable 1106B provides an opposing force to the detection element including detection pulley 1120B and plunger 1124B that is pushed against cable 1106B in a direction indicated by arrow 1132B, due to plunger 1124B being forced by spring 1128B in that direction. This results in a first configuration (first position) of the detection element including pulley 1120B and plunger 1124B while the cable 1106B in unbroken and/or without slack. Detection pulley 1120B rotates as cable 1106B moves.

In response to breakage or slackening of cable 1106A, the opposing force from cable 1106A is reduced or removed and the detection element including plunger 1124A is allowed to move further in direction 1132A. Magnet 1126A in plunger 1124A changes position along with the detection element, and this change in position is sensed by magnetic sensor 1130. If the sensed change in position is over a threshold amount, or a threshold position of the detection element is reached (e.g., the change in position flips the magnetic field sensing switch of magnetic sensor 1130), a signal is sent by the magnetic sensor 1130 to a control circuit as an alert that the cable has lost tension or has broken.

Similarly, in response to breakage or slackening of cable 1106B, the detection element including plunger 1124B is allowed to move further in direction 1132B. Magnet 1126B in plunger 1124B changes position to a second configuration (second position), and this new position (e.g., change in position) is sensed by magnetic sensor 1130. If the sensed change in position is over a threshold amount, or a threshold position of the detection element is reached (e.g., the change in position flips the magnetic field sensing switch of magnetic sensor 1130), a signal is sent by the magnetic sensor 1130 to a control circuit as an alert that the cable has broken (or has lost tension).

In some implementations or cases, breaking of one of cables 1106A or 1106B causes slackening of the other cable 1106B or 1106A, e.g., if the cables 1106A and 1106B are different portions of a single cable, such that cable breakage or slackening is detected on both cables 1106A and 1106B by the detection device 1100.

In some implementations, detection pulleys 1120A and 1120B can be omitted or replaced with one or more other features that contact the cable 1106. In some implementations, other types of sensors can be used in place of or in addition to magnetic sensor 1130. For example, one or more optical sensors, potentiometers, or other sensors can be used to detect movement of the detection elements including plungers 1124A and 1124B.

Figure 12:
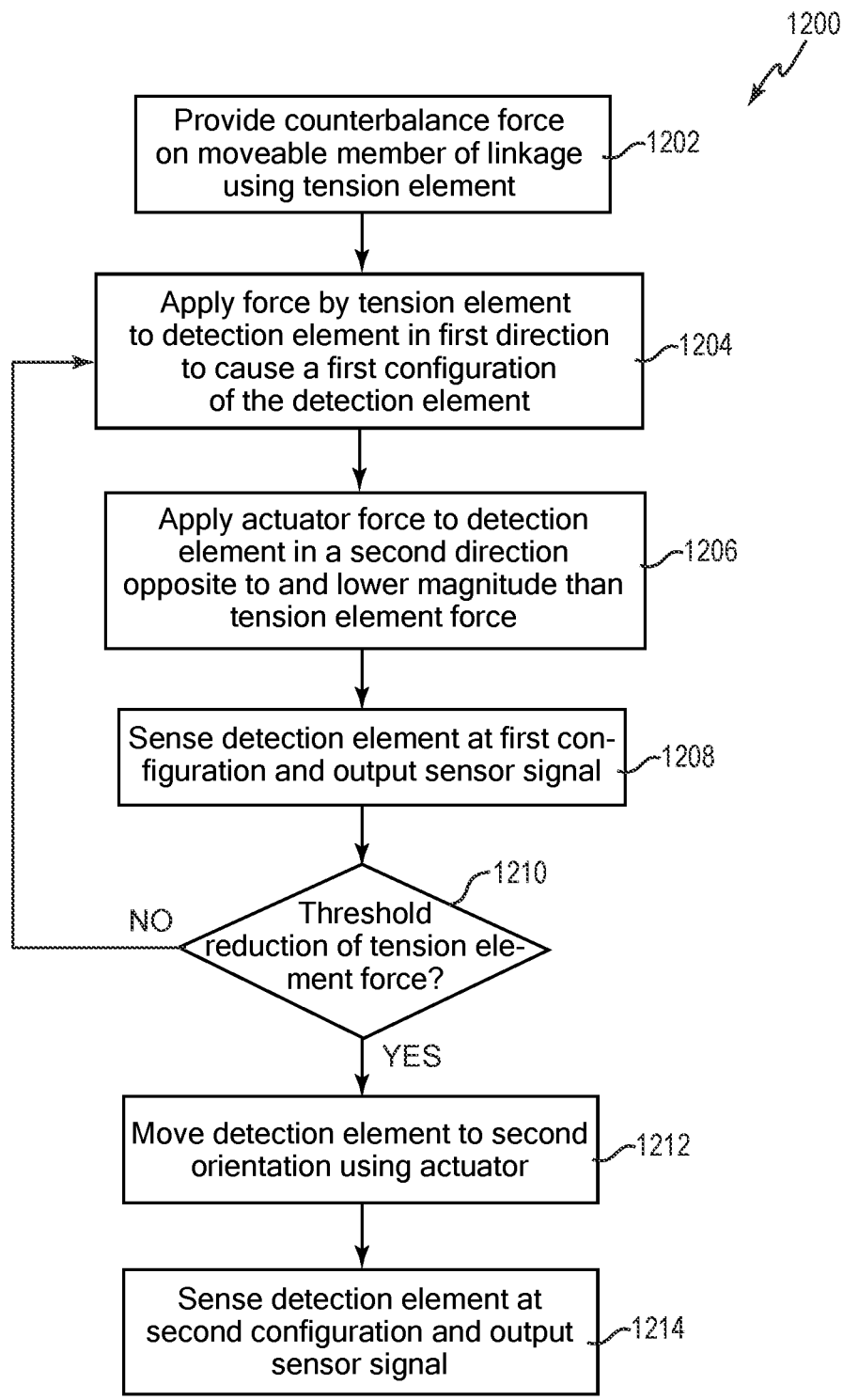
FIG. 12 is a flow diagram illustrating an example method to detect breakage of a tension element in a counterbalance mechanism, according to some implementations.

FIG. 12 is a flow diagram illustrating an example method 1200 to detect a break of a tension element in a counterbalance mechanism, according to some implementations. Method 1200 can, for example, be used with any of the example counterbalance mechanisms described herein or other counterbalance mechanisms. In some implementations, the counterbalance mechanism is coupled to or included in a mechanical arm, such as an arm included in a user control system 1302 of FIG. 13, and sensor signal output provided by method 1200 can be received by a control circuit component of the user control system 1302. In some examples, the control circuit can include one or more processors, e.g., microprocessors or other circuits, some examples of which are described below with reference to FIG. 15. Other implementations can use a counterbalance mechanism provided in other types of mechanical systems, e.g., non-teleoperated systems.

In block 1202, a counterbalance force is provided on a moveable member using a tension element of the counterbalance mechanism. For example, the moveable member can be a member of a linkage. In some examples, the tension element can be a cable wrapped around one or more tension pulleys and connected to a cable break detection pulley as described in various implementations herein. The tension element provides force on the member opposing gravity.

In block 1204, a force is applied to a detection element by the tension element in a first direction to cause a first configuration of the detection element. In some example implementations, the detection element includes a detection pulley and the tension element force is a tension element torque applied to the detection pulley in a first rotational direction via the tension element. As described herein, the detection pulley can be forced against a first stop as impelled by such tension element torque, such that the first stop stops the detection pulley at the first configuration that is a first orientation. In some other example implementations, the detection element includes a linear member such as a plunger and the tension element force is a first linear force opposing motion of the linear member in a linear degree of freedom (e.g., FIGS. 11A-11B) such that the detection element is in the first configuration that is a first position.

In block 1206, an actuator force is applied to the detection element in a second direction that is opposite to and lower in magnitude than the tension element force of block 1204. As described in various implementations, the actuator force can be provided by an actuator such as a spring (e.g., torsion spring or helical spring). The actuator force has a lower magnitude than the tension element force such that the detection element is provided in the first configuration as caused by the tension element force. Thus, the actuator force does not move the detection element in the opposing direction. Block 1206 can be performed simultaneously to block 1204, e.g., the actuator force can be applied to the detection element prior to and/or during the application of the tension element force.

In some example implementations, the detection element includes a detection pulley and the actuator force is a torque applied to the detection pulley in a second rotational direction by the actuator. In some example implementations, the detection element includes a linear member such as a plunger and the actuator force is a second linear force applied to the linear member in the opposite direction to the first linear force in the linear degree of freedom (e.g., FIGS. 11A-11B).

In block 1208, the detection element is sensed at the first configuration by a sensor, and, in some implementations, the sensor sends a sensor signal that indicates the sensing of the detection element at the first configuration. For example, the sensor signal can be sent to a control circuit as described herein. In some implementations, a sensor signal is not sent, e.g., the first configuration is assumed as a default configuration.

In block 1210, if at least a threshold reduction (or greater) in the magnitude of the tension element force applied in block 1204 has occurred relative to the magnitude of the actuator force applied to the detection element in block 1206, the process continues to block 1212. For example, the threshold reduction can be a particular magnitude of force reduction that results in the tension element force having a magnitude less than the magnitude of the actuator force. This reduction in the tension element force occurs in response to a break in the tension element, thus reducing the force on the detection element from the tension element.

If the threshold reduction in the tension element force has not occurred in block 1210, the process returns to block 1204 such that the detection element remains at the first configuration.

In block 1212, which is performed in response to the threshold reduction in magnitude of the tension element force, the detection element is moved to a second configuration by the actuator. The tension element force has been reduced to a magnitude sufficient to allow the actuator force to move the detection element in its actuated direction and impel the detection element to the second configuration. In some implementations, the detection element remains in the second configuration while the reduction in tension element force exists. In some example implementations, the actuator force rotates a detection pulley in the second rotational direction to a second rotational orientation, where it is stopped against a second stop. In other example implementations, the actuator force translates a linear member in the second linear direction to a second position.

In block 1214, the detection element is detected at the second configuration by the sensor, and the sensor sends a sensor signal that indicates the detection of the second configuration. For example, the sensor signal can be sent to the control circuit as described above.

In various implementations, the system including the counterbalance mechanism can perform various actions in response to receiving the sensor signal that indicates that the detection element is in the second configuration. For example, this sensor signal indicates a state in which the counterbalance mechanism is no longer providing gravity compensation or is providing reduced gravity compensation, which may cause undesired forces on or movement of in a control input device coupled to the counterbalance mechanism. In some examples, the control circuit, in response to receiving such a sensor signal, can immediately deactivate a controlling mode in which the control input device controls a slave device and activate a non-controlling mode in which the control input device no longer controls the slave device, so that the slave device does not move in an uncontrolled and undesired manner. In some implementations, the system can deactivate actuators outputting force on the control input device in response to receiving such a sensor signal.

It should be noted that the blocks described in the methods disclosed herein can be performed in a different order than shown and/or simultaneously (partially or completely) with other blocks, where appropriate. For example, blocks 1202, 1204, 1206, and/or 1208 can be performed partially or completely simultaneously. Further, not all of the described blocks need be performed in various implementations. In some implementations, blocks can be performed multiple times, in different orders, and/or at different times in the methods.

Figure 13:
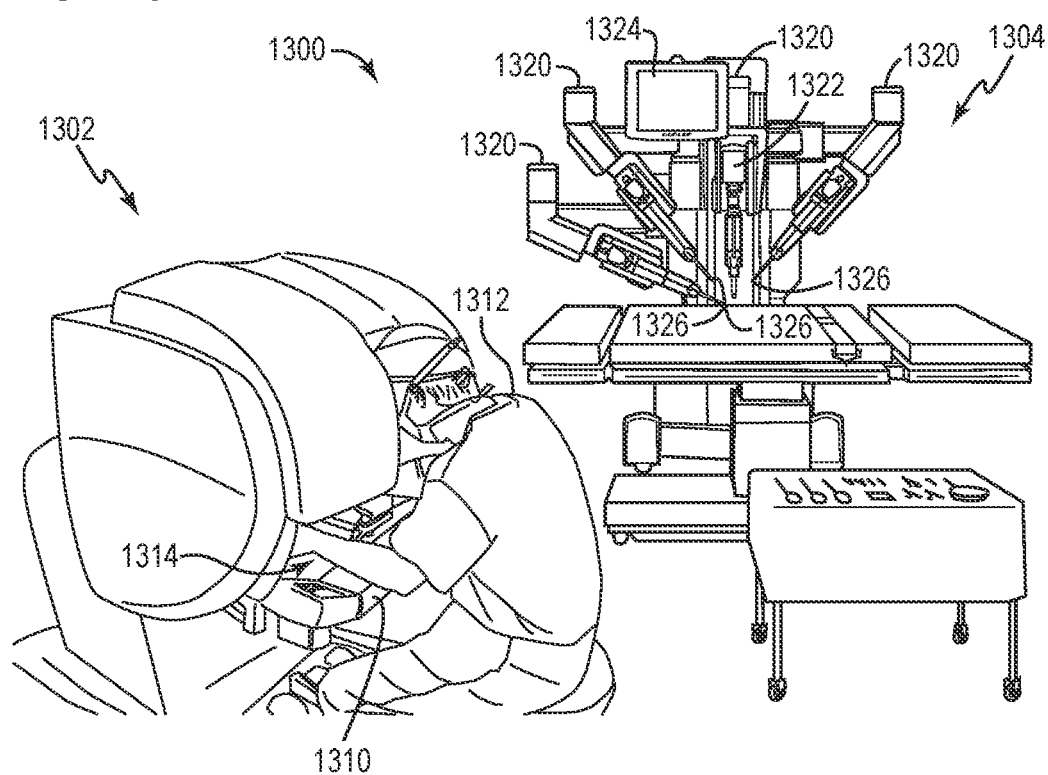
FIG. 13 is a diagrammatic illustration of an example implementation of a teleoperated surgical system which can be used with one or more features disclosed herein, according to some implementations.

FIG. 13 is a diagrammatic illustration of an example teleoperated surgical system 1300 which can be used with one or more features disclosed herein. Other types of control systems and/or master-slave systems can be used in other implementations involving described features. Teleoperated surgical system 1300 includes a user control system (e.g., surgeon's console) 1302 and a manipulator system 1304.

In this example, the user control system 1302 includes a viewer 1413 (shown in FIG. 14) where an image of a worksite is displayed during an operating procedure using the system 1300. For example, the image can be displayed by a display device such as one or more display screens, depict a surgical site during a surgical procedure. A support 1310 is provided on which a user 1312, e.g., an operator such as a surgeon, can rest his or her forearms while gripping two control input devices 1410 and 1412 (shown in FIG. 14), one in each hand. The control input devices are positioned in a workspace 1314 disposed inwardly beyond the support 1310. When using the control system 1302, the user 1312 can sit in a chair in front of the user control system, position his or her eyes in front of the viewer 1413 and grip the control input devices, one in each hand.

A manipulator system 1304 is also included in teleoperated system 1300. For example, manipulator system 1304 can include a manipulator device or slave device in this example, or can alternatively be a different type of device. In some implementations, during a surgical procedure, manipulator system 1304 can be positioned close to a patient (or simulated patient) for surgery at a surgical site, where its base can remain stationary until a particular surgical procedure or stage of a procedure is completed. Manipulator system 1304 can include one or more manipulator arm assemblies 1320. In some examples, one or more of the arm assemblies 1320 can be configured to hold an image capturing device, e.g., an endoscope 1322, which can provide captured images of a portion of the surgical site. In some implementations, the captured images can be transmitted to viewer 1413 of the user control system 1302 and/or transmitted to one or more other displays, e.g., a display 1324 coupled to the manipulator system 1304. In some examples, each of the other arm assemblies 1320 may include a surgical tool 1326. Each surgical tool 1326 can include a surgical end effector, e.g., for treating tissue of a patient. For example, an arm assembly 1320 can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. One example of a surgical manipulator arm is a da Vinci® surgical system instrument manipulator arm in surgical systems commercialized by Intuitive Surgical Operations, Inc. of Sunnyvale, California.

In this example, the arm assemblies 1320 can be caused to move and articulate the surgical tools 1326 in response to manipulation of the control input devices 1410 and 1412 at the workstation 1302 by the user 1312, e.g., so that the user 1312 can direct surgical procedures at internal surgical sites through minimally invasive surgical apertures. For example, one or more actuators coupled to the arm assemblies 1320 can output force to cause links or other portions of the arm assemblies to move in particular degrees of freedom in response to control signals received from the user control system 1302. In some examples, movement of an arm and end effector in one or more degrees of freedom can correspond to (e.g., follow) movement in one or more degrees of freedom of an associated control input device handle by a user. The user control system 1302 can be used within a room (e.g., an operating room) with the manipulator system 1304 or can be positioned more remotely from the manipulator system 1302, e.g., at a different location than the manipulator system. One or more of the arm assemblies 1320 can include counterbalance mechanisms to compensate for a force of gravity, e.g., similar to any of the counterbalance mechanisms described herein, and these counterbalance mechanisms can include tension element breakage detection features described herein.

Some implementations of the teleoperated system 1300 can provide different modes of operation. In some examples, in a non-controlling mode (e.g., safe mode) of the teleoperated system 1300, the controlled motion of the manipulator system 1304 is disconnected from the control input devices of the user control system 1302 in disconnected configuration, such that movement and other manipulation of the control input devices does not cause motion of the manipulator system 1304. In a controlling mode of the teleoperated system (e.g., following mode, in which one or more slave manipulators follow a corresponding control input device), motion of the manipulator system 1304 can be controlled by the control input devices 1410 and 1412 of the user control system 1302 such that movement and other manipulation of the control input devices causes motion of the manipulator system 1304, e.g., during a surgical procedure.

Some implementations can be or include a teleoperated medical system such as a da Vinci® Surgical System (e.g., a Model IS3000 or IS4000, marketed as the da Vinci Si® or da Vinci Xi® Surgical System), commercialized by Intuitive Surgical, Inc. of Sunnyvale, California. Features disclosed herein may be implemented in various ways, including in implementations at least partially computer-controlled, controlled via electronic control signals, manually controlled via direct physical manipulation, etc. Implementations on da Vinci® Surgical Systems are merely exemplary and are not to be considered as limiting the scope of the features disclosed herein. For example, different types of teleoperated systems having slave devices at worksites can make use of actuated controlled features described herein. Teleoperated or non-teleoperated systems can use one or more described features, e.g., various types of control systems and devices, peripherals, etc.

In some implementations, a controlled manipulator system can be a virtual representation of device, e.g., presented in a graphical simulation provided by a computing device coupled to the teleoperated system 1300. For example, a user can manipulate the control input devices 1410 and 1412 of the user control system 1302 to control a displayed representation of an end effector in virtual space of the simulation, similarly as if the end effector were a physical object coupled to a physical slave device.

Figure 14:
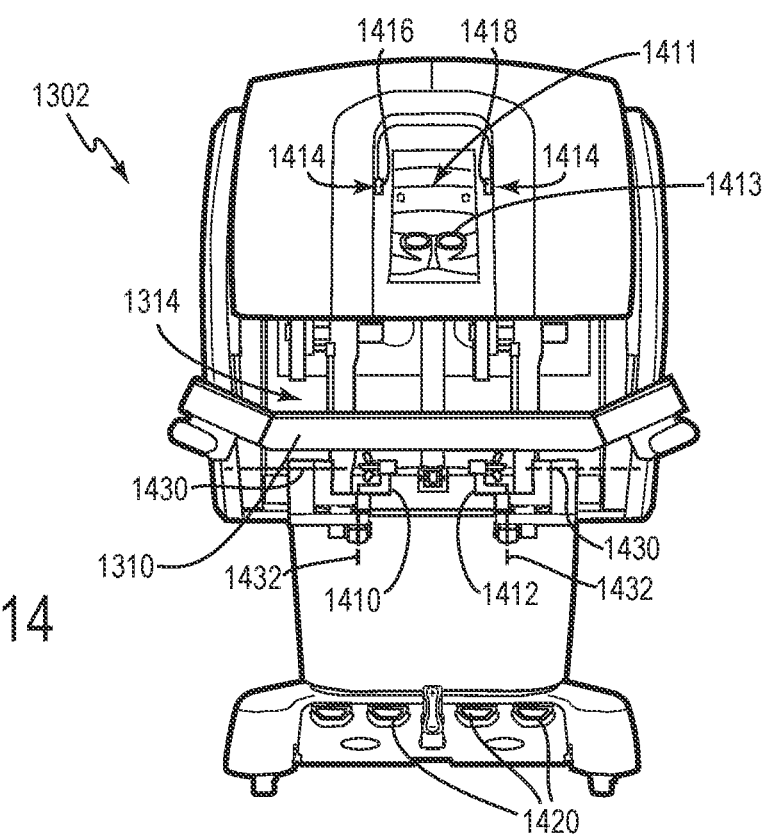
FIG. 14 is a front elevational view of an example user control system as shown in FIG. 13, according to some implementations.

FIG. 14 is a front elevational view of an example user control system 1302 as described above for FIG. 13. User control system 1302 includes a viewer 1413, and an image of a worksite can be displayed during a procedure using the teleoperated system 1300. For example, images depicting a surgical site can be displayed during a surgical procedure. The viewer 1413 can be positioned within a viewing recess 1411 in which the user can position his or her head to view images displayed by the viewer 1413. When using the user control system 1302, the user 1312 can sit in a chair in front of the user control system and position his or her head within the recess 1411 such that his or her eyes are positioned in front of the viewer 1413.

In some implementations, one or more user presence sensors 1414 can be positioned at one or more locations of the user control system 1302 to detect the presence of a user located next to or near to the user control system 1302. In this example, the user presence sensors 1414 can sense a presence of a user's head within the recess 1411.

Two control input devices 1410 and 1412 are provided for user manipulation. In some implementations, each control input device 1410 and 1412 can be configured to control motion and functions an associated arm assembly 1320 of the manipulator system 1304. In some examples, the control input devices are master devices and manipulator system 104 is a slave device in a master-slave control relationship. For example, a control input device 1410 or 1412 can be moved in a plurality of degrees of freedom to move a corresponding end effector of the manipulator system 1304 in corresponding degrees of freedom. The control input devices 1410 and 1412 are positioned in workspace 1314 inwardly beyond the support 1310. For example, a user 1312 can rest his or her forearms while gripping the two control input devices 1410, 1412, with one control input device in each hand. The user also positions his or her head within the viewing recess 1411 to view the viewer 1413 as described above while manipulating the control input devices 1410 and 1412. The control input devices may include any number of a variety of input devices manipulable by the user, such as kinematically linked (mechanically grounded) hand grips, finger grips, joysticks, trackballs, data gloves, trigger-guns, hand-operated controllers, voice recognition devices, touch screens, and the like.

In some implementations, the control input devices are manual input devices which move in all six Cartesian degrees of freedom, including motion about axes 1430 and 1432. Control input devices 1410 and 1412 may also include an actuatable grip portion (e.g., handle) for actuating corresponding instruments of a manipulator system, e.g., for closing grasping jaws, applying an electrical potential to an electrode, delivering a medicinal treatment, and the like. In some implementations, a grip function, such as moving two grip portions of a control input device together and apart in a pincher movement, can provide an additional mechanical degree of freedom (i.e., a grip DOF). In some example implementations, control input devices 1410 and 1412 may provide control of one or more surgical instruments 1326 in a surgical environment or proxy surgical instruments in a virtual environment. Some implementations of user control system 1302 can include one or more foot controls 1420 positioned below the control input devices 1410 and 1412, e.g., to input various commands to the teleoperated system while the user is operating the user control system 1302.

Some example implementations of disclosed features follow.

In some implementations, a mechanism to detect breakage of a tension element such as a cable is included in a counterbalance mechanism, and the counterbalance mechanism is included in a component of a teleoperated medical system that has a mechanical linkage. The mechanism includes a moveable detection element, e.g., a detection pulley rotatably coupled to a first member of the mechanical linkage. The detection pulley is rotatable about its axis of rotation between a first orientation and a second orientation in its range of motion. The tension element is coupled between the first member and a second member of the mechanical linkage, has an end coupled to the detection pulley, and applies a first torque to the detection pulley in a first rotational direction to bias the detection pulley toward the first orientation. An actuator is coupled between the detection pulley and the first member, and generates a second torque on the detection pulley in a second rotational direction toward the second orientation of the detection pulley. The mechanism includes a pulley orientation sensor which senses a change of the detection pulley from the first orientation to the second orientation.

In some implementations, a method to detect breakage of a tension element coupled to a counterbalance spring in a counterbalance mechanism includes applying, by the tension element, a first force to a detection element in a first direction to cause a first configuration of the detection element. The method includes applying, by an actuator, a second force to the detection element in a second direction opposite to the first direction, and causing, by the second force, the detection element to move to a second configuration in response to at least a threshold reduction of the first force caused by breaking of the tension element. The method includes sensing a change of the detection element from the first configuration to the second configuration. In various examples, the detection element is a detection pulley, the first and second forces are first and second torques, respectively, and the first and second configurations are first and second orientations of the detection pulley, respectively. In further examples, the detection element includes a pulley rotatably coupled to a linear member, applying the first force includes applying a first linear force to the detection element at a first position in a first linear direction, applying the second force includes applying a second linear force to the linear member in a second linear direction opposite to the first linear direction to bias the detection element toward a second position, the detection element is caused to linearly move to the second position in a linear range of motion in response to at least a threshold reduction of the first linear force caused by the breaking of the tension element, and a change in position of the detection element from the first position to the second position is sensed. A counterbalance force can be provided on a moveable member of a linkage by the tension element.

Figure 15:
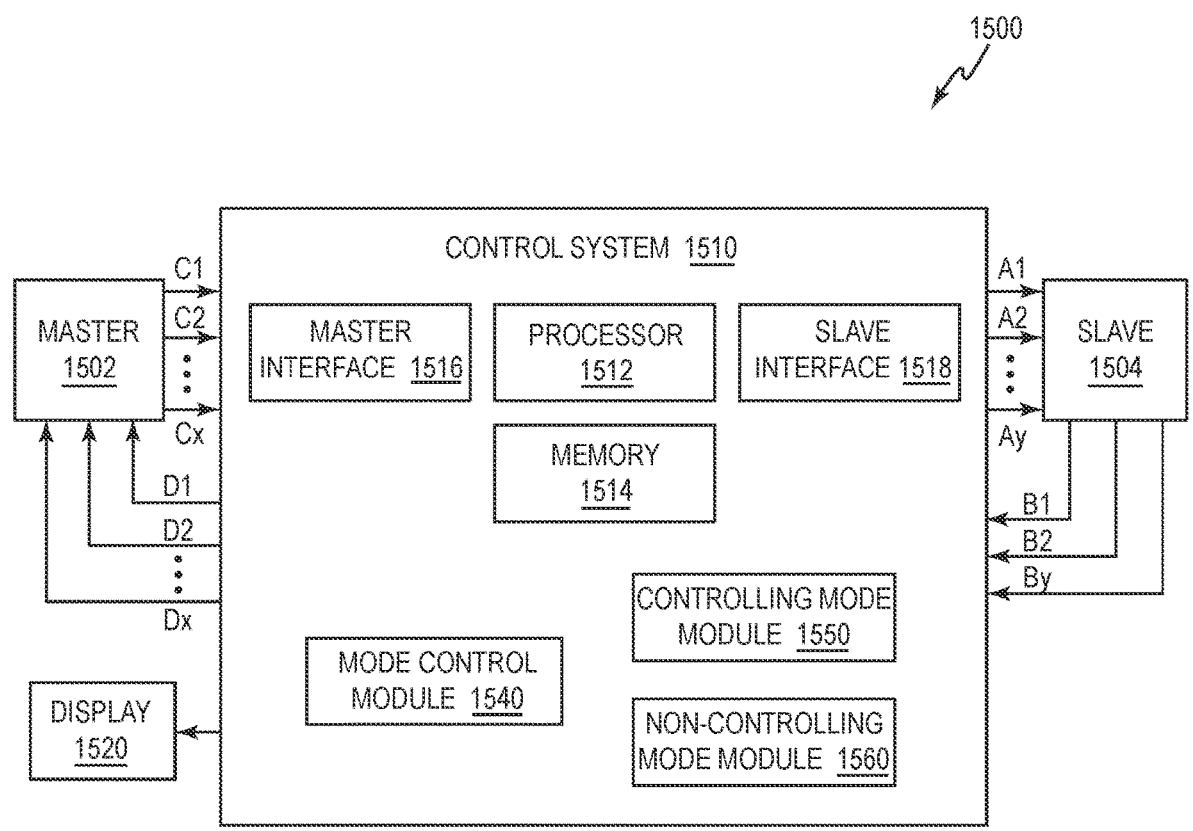
FIG. 15 is a block diagram of an example master-slave system which can be used in one or more implementations described herein.

FIG. 15 is a block diagram of an example master-slave system 1500 which can be used with one or more features described herein. System 1500 includes a master device 1502 that a user may manipulate in order to control a slave device 1504 in communication with the master device 1502. In some implementations, master device 1502 can be, or can be included in, user control system 1302 of FIG. 13. In some implementations, slave device 1504 can be, or can be included in, manipulator system 1304 of FIG. 13. More generally, master device 1502 can be, or be a portion of, any type of control input device that can be physically manipulated by a user. Master device 1502 generates control signals C1 to Cx indicating positions, states, and/or changes of one or more master control devices in their degrees of freedom. The master device 1502 can also generate control signals (not shown) indicating selection of physical buttons and other manipulations by the user.

A control block 1510 can be included in the master device 1502, in the slave device 1504, or in a separate device, e.g., an intermediary device between master device 1502 and slave device 1504. In some implementations, the control block 1510 can be distributed among multiple of these devices. Control block 1510 receives control signals C1 to Cx and generates actuation signals A1 to Ay, which are sent to slave device 1504. Control block 1510 can also receive sensor signals B1 to By from the slave device 1504 that indicate positions, states, and/or changes of various slave components (e.g., manipulator arm members, instruments, or other elements). Control block 1510 can include general components such as a processor 1512, memory 1514, and interface hardware 1516 and 1518 for communication with master device 1502 and slave device 1504, respectively. Processor 1512 can execute program code and control basic operations of the system 1500, including functions related to sensing orientations of arm members and sending signals to control motors as described herein, and can include one or more processors of various types, including microprocessors, application specific integrated circuits (ASICs), and other electronic circuits. Memory 1514 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control block 1510, e.g., display(s) 1520 such as the viewer 1513 of the user control system 1302 and/or display 1324 of FIGS. 13 and 14.

In this example, control block 1510 includes a mode control module 1540, a controlling mode module 1550, and a non-controlling mode module 1560. Other implementations can use other modules, e.g., a force output control module, sensor input signal module, etc. In some implementations, the modules 1540, 1550, and 1560 can be implemented using the processor 1512 and memory 1514, e.g., program instructions stored in memory 1514 and/or other memory or storage devices connected to control block 1510.

Mode control module 1540 can detect when a user initiates a controlling mode and a non-controlling mode of the system, e.g., by user selection of controls, sensing a presence of a user at a user control system or control input device, sensing required manipulation of a control input device, etc. The mode control module can set the controlling mode or a non-controlling mode of the control system 1510 based on one or more control signals C1 to Cx.

In some implementations, controlling mode module 1550 may be used to control a controlling mode of control block 1510. Controlling mode module 1550 can receive control signals C1 to Cx and can generate actuation signals A1 to Ay that control actuators of the slave device 1504 and cause it to follow the movement of master device 1502, e.g., so that the movements of slave device 1504 correspond to a mapping of the movements of master device 1502. Controlling mode module 1550 can also be used to control forces on the master device 1502, e.g., forces output on one or more components of the arm assembly of the master device, e.g., base member, arm members, grip members, etc., using one or more control signals D1 to Dx output to actuator(s) used to apply forces to the components, e.g., on arm links of the arm 302, to link members and/or grip members of the control input device 304, etc. In some examples, control signals D1 to Dx can be used to provide force feedback, gravity compensation, etc.

In some implementations, a non-controlling mode module 1560 may be used to control a non-controlling mode of system 1500. In the non-controlling mode, movement in one or more degrees of freedom of master device 1502, or other manipulations of master device 1502, has no effect on the movement of one or more components of slave device 1504. In some implementations, non-controlling mode can include one or more other operating modes of the control block 1510, e.g., a selection mode in which movement of a control input device of master device 1502 in one or more of its degrees of freedom and/or selection of the control switches of the control input device can control selection of displayed options, e.g., in a graphical user interface displayed by display device 1520 and/or other device. A viewing mode can allow movement of the control input device to control a display provided from cameras, or movement of cameras, that may not be included in the slave device 1504. Control signals C1 to Cx can be used by the non-controlling mode module 1560 to control such elements (e.g., cursor, views, etc.) and control signals D1 to Dx can be determined by the non-controlling mode module to cause output of forces on the master control device during such non-controlling modes, e.g., to indicate to the user interactions or events occurring during such modes.

Some implementations described herein, e.g., method 1200, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A tension element breakage detection mechanism comprising:
   a tension element, wherein a load is applied to the tension element;
   a moveable detection element contacting the tension element, the moveable detection element being positionable, by the tension element, in a first configuration in a range of motion of the moveable detection element;
   an actuator coupled to the moveable detection element, the moveable detection element being positionable in a second configuration in the range of motion of the moveable detection element by a bias applied by the actuator, the bias being independent from presence of the load, wherein under the load the tension element counters the bias of the actuator to maintain the moveable detection element in the first configuration; and
   a sensor arranged to detect a change of the moveable detection element from the first configuration to the second configuration in the range of motion of the moveable detection element, the change being in response to the tension element no longer countering the bias of the actuator.

2. The tension element breakage detection mechanism of claim 1, wherein:
   the tension element is coupled to a counterbalance spring.

3. The tension element breakage detection mechanism of claim 2, wherein:
   the tension element has a first end coupled to the counterbalance spring and the tension element has a second end coupled to the moveable detection element.

4. The tension element breakage detection mechanism of claim 2, wherein:
   the load is moveably coupled to the moveable detection element; and
   the load includes at least one mechanical member of a mechanical arm.

5. The tension element breakage detection mechanism of claim 2, wherein:
   the tension element is a cable including two doubled portions provided between the counterbalance spring and the moveable detection element.

6. The tension element breakage detection mechanism of claim 2, further comprising:
   a tension pulley around which the tension element is at least partially wrapped, the tension pulley positioned between the counterbalance spring and the moveable detection element in a path of the tension element.

7. The tension element breakage detection mechanism of claim 2, wherein:
   the actuator is a spring that is different than the counterbalance spring.

8. The tension element breakage detection mechanism of claim 1, wherein:
   the tension element breakage detection mechanism is embodied in a counterbalance apparatus included in a component of a teleoperated surgical system.

9. The tension element breakage detection mechanism of claim 1, wherein:
   the tension element is a cable;
   the moveable detection element includes a detection pulley; and
   the cable is coupled to the detection pulley and causes rotation of the detection pulley in response to movement of the cable along a lengthwise axis of the cable.

10. The tension element breakage detection mechanism of claim 1, wherein:
    the tension element counters the bias of the actuator while the tension element is in an unbroken state, wherein the first configuration is a first orientation or a first position in the range of motion of the moveable detection element, wherein the moveable detection element remains in the first orientation or the first position while the tension element is in the unbroken state, and
    the tension element no longer counters the bias of the actuator in response to a breakage of the tension element.

11. The tension element breakage detection mechanism of claim 10, wherein:
    the moveable detection element includes a detection pulley;
    the first configuration is a first orientation of the detection pulley about a rotational axis of the detection pulley;
    the second configuration is a second orientation of the detection pulley about the rotational axis of the detection pulley.

12. The tension element breakage detection mechanism of claim 11, wherein:
    the tension element is a cable;
    the detection pulley remains at the first orientation while the cable is in an unbroken state; and
    the detection pulley is at the second orientation in response to the tension element no longer countering the bias of the actuator.

13. The tension element breakage detection mechanism of claim 10, wherein:
    the moveable detection element is moved to the second configuration on condition of at least a threshold reduction of a first force provided by the tension element on the moveable detection element caused by breaking of the tension element; and
    the threshold reduction of the first force is such that the first force has a magnitude less than a magnitude of a second force provided by the actuator.

14. The tension element breakage detection mechanism of claim 1, wherein:
    the moveable detection element is rotatably coupled to a first member of a mechanical linkage;
    the tension element is coupled between the first member and a second member of the mechanical linkage; and
    the load is coupled to the moveable detection element, the load including at least one member of the mechanical linkage.

15. The tension element breakage detection mechanism of claim 1, wherein:
    the tension element breakage detection mechanism further includes a first member, a second member coupled to the first member, a counterbalance spring coupled to the first member, and a tension pulley rotatably coupled to the second member;

the moveable detection element is a detection pulley that is rotatably coupled to the first member;

the actuator is coupled between the detection pulley and the first member;

the tension element has a first end coupled to the counterbalance spring and a second end coupled to the detection pulley;

the tension element is coupled between the first member and the second member;

the tension element is wrapped around at least a portion of the tension pulley and wrapped around at least a portion of the detection pulley; and the tension element applies a counterbalance force on the second member.

16. The tension element breakage detection mechanism of claim 1, wherein:

a first stop is positioned in the range of motion of the moveable detection element against which the moveable detection element is biased at the first configuration; and a second stop is positioned in the range of motion of the moveable detection element against which the moveable detection element is biased at the second configuration.

17. The tension element breakage detection mechanism of claim 1, wherein:

the moveable detection element includes a linear member;

the linear member is coupled to the actuator; and the moveable detection element has a linear range of motion.

18. The tension element breakage detection mechanism of claim 1, wherein:

the moveable detection element includes a pulley and a linear member;

the pulley is rotatably coupled to the linear member and the pulley is pushed against the tension element by the bias applied by the actuator;

the linear member is coupled to the actuator; and the moveable detection element has a linear range of motion.

19. The tension element breakage detection mechanism of claim 18, wherein:

the actuator generates a linear force on the linear member;

the tension element, in an unbroken state, contacts the pulley; and the tension element biases the moveable detection element by opposing the linear force generated by the actuator to cause the linear member to be positioned in the first configuration.

20. The tension element breakage detection mechanism of claim 19, wherein:

an opposing force is applied to the moveable detection element via the tension element, the opposing force biasing the moveable detection element toward the first configuration in the linear range of motion of the moveable detection element;

the linear force causes the moveable detection element to move to the second configuration on condition of at least a threshold reduction of the opposing force caused by breaking of the tension element; and the threshold reduction of the opposing force is such that the opposing force has a magnitude less than a magnitude of the linear force.

* * * * *